(12) United States Patent
Heim et al.

(10) Patent No.: US 8,357,155 B2
(45) Date of Patent: *Jan. 22, 2013

(54) MULTIELECTRODE ELECTROSURGICAL BLADE

(75) Inventors: Warren P. Heim, Boulder, CO (US); James L. Brassell, Boulder, CO (US)

(73) Assignee: Microline Surgical, Inc., Beverly, MA (US)

(*) Notice: Subject to any disclaimer, the term of this patent is extended or adjusted under 35 U.S.C. 154(b) by 1737 days.

This patent is subject to a terminal disclaimer.

(21) Appl. No.: 11/427,652

(22) Filed: Jun. 29, 2006

(65) Prior Publication Data

US 2006/0241588 A1 Oct. 26, 2006

Related U.S. Application Data

(63) Continuation-in-part of application No. 11/185,668, filed on Jul. 20, 2005, now abandoned.

(60) Provisional application No. 60/695,692, filed on Jun. 30, 2005, provisional application No. 60/589,508, filed on Jul. 20, 2004.

(51) Int. Cl.
*A61B 18/14* (2006.01)

(52) U.S. Cl. .......................... 606/45; 606/41

(58) Field of Classification Search ................ 606/41, 606/45, 50, 48

See application file for complete search history.

(56) References Cited

U.S. PATENT DOCUMENTS

| | | | |
|---|---|---|---|
| 874,178 A | 12/1807 | DeForest | |
| 1,713,970 A | 5/1929 | Lowrey et al. | |
| 1,814,791 A | 7/1931 | Ende | |
| 3,799,168 A | 3/1974 | Peters | |
| 3,970,088 A | 7/1976 | Morrison | |
| 3,987,795 A | 10/1976 | Morrison | |
| 4,033,351 A * | 7/1977 | Hetzel | 606/48 |
| 4,043,342 A * | 8/1977 | Morrison, Jr. | 606/48 |
| 4,074,718 A | 2/1978 | Morrison, Jr. | |
| 4,161,950 A | 7/1979 | Doss et al. | |

(Continued)

FOREIGN PATENT DOCUMENTS

EP 1566645 8/2005

(Continued)

OTHER PUBLICATIONS

Serway, Raymond; Physics for Scientists and Engineers; Thomson Brooks/Cole, Belmont, CA; 2004; pp. 746-755.

(Continued)

*Primary Examiner* — Michael Peffley
*Assistant Examiner* — Samantha Good
(74) *Attorney, Agent, or Firm* — Greenblum & Bernstein, P.L.C.

(57) ABSTRACT

An electrosurgical instrument blade includes a body having more than two electrodes with at least two electrodes having alternating current power supplied to them provide a bipolar alternating current configuration and employ a means other than electrode spacing for reducing or preventing accumulation of eschar. The electrodes are separated from each other using electrically insulating materials such that electric current does not flow between at least two of the bipolar alternating current electrodes unless they contact at least one other electrically conductive medium, such as patient tissue. The conductor edge portion and insulation layer each have geometric shapes and composition to reduce or eliminate the production of smoke and eschar and reduce tissue damage. The outer profile of the insulation layer and conductive element are configured to facilitate the flow of electrosurgical decomposition products away from the conductor edge where they are formed.

40 Claims, 18 Drawing Sheets

U.S. PATENT DOCUMENTS

| | | | |
|---|---|---|---|
| 4,202,337 A | 5/1980 | Hren et al. | |
| 4,228,800 A | 10/1980 | Degler, Jr. et al. | |
| 4,248,231 A | 2/1981 | Herczog et al. | |
| 4,314,559 A | 2/1982 | Allen | |
| 4,333,467 A | 6/1982 | Domicone | |
| 4,449,926 A | 5/1984 | Weiss | |
| 4,481,057 A | 11/1984 | Beard | |
| 4,492,231 A | 1/1985 | Auth | |
| 4,534,347 A | 8/1985 | Taylor | |
| 4,545,375 A | 10/1985 | Cline | |
| 4,565,200 A | 1/1986 | Cosman | |
| 4,589,411 A | 5/1986 | Friedman | |
| 4,622,966 A | 11/1986 | Beard | |
| 4,657,016 A | 4/1987 | Garito et al. | |
| 4,785,807 A | 11/1988 | Blanch | |
| 4,793,346 A | 12/1988 | Mindich | |
| 4,823,791 A | 4/1989 | D'Amelio et al. | |
| 4,848,337 A | 7/1989 | Shaw et al. | |
| 4,926,243 A * | 5/1990 | Nakagawa et al. | 257/659 |
| 4,931,047 A | 6/1990 | Broadwin et al. | |
| 4,976,711 A | 12/1990 | Parins et al. | |
| 5,015,227 A | 5/1991 | Broadwin et al. | |
| 5,030,218 A | 7/1991 | Alexander | |
| 5,080,660 A | 1/1992 | Buelna | |
| 5,160,334 A | 11/1992 | Billings et al. | |
| 5,167,659 A | 12/1992 | Ohtomo et al. | |
| 5,267,994 A | 12/1993 | Gentelia et al. | |
| 5,308,311 A | 5/1994 | Eggers et al. | |
| 5,314,459 A * | 5/1994 | Swanson et al. | 607/122 |
| 5,318,562 A | 6/1994 | Levy et al. | |
| 5,318,563 A | 6/1994 | Malis et al. | |
| 5,370,645 A | 12/1994 | Klicek et al. | |
| 5,380,320 A | 1/1995 | Morris | |
| 5,382,247 A | 1/1995 | Cimino et al. | |
| 5,464,390 A | 11/1995 | Arnett et al. | |
| 5,472,442 A | 12/1995 | Klicek | |
| 5,472,443 A | 12/1995 | Cordis et al. | |
| 5,520,684 A | 5/1996 | Imran | |
| 5,540,681 A | 7/1996 | Strul et al. | |
| 5,549,604 A | 8/1996 | Sutcu | |
| 5,554,172 A | 9/1996 | Horner et al. | |
| 5,633,578 A | 5/1997 | Eggers et al. | |
| 5,643,256 A | 7/1997 | Urueta | |
| 5,693,045 A | 12/1997 | Eggers et al. | |
| 5,693,050 A | 12/1997 | Speiser | |
| 5,697,909 A | 12/1997 | Eggers et al. | |
| 5,697,926 A | 12/1997 | Weaver | |
| 5,702,387 A | 12/1997 | Arts et al. | |
| 5,707,402 A | 1/1998 | Heim | |
| 5,713,895 A | 2/1998 | Lontine et al. | |
| 5,766,153 A | 6/1998 | Eggers et al. | |
| 5,833,686 A | 11/1998 | Zhao | |
| 5,836,943 A | 11/1998 | Miller | |
| 5,891,095 A | 4/1999 | Eggers et al. | |
| 6,030,218 A | 2/2000 | Robinson | |
| 6,039,735 A | 3/2000 | Greep | |
| 6,059,783 A | 5/2000 | Kirwan | |
| 6,066,137 A | 5/2000 | Greep | |
| 6,074,387 A | 6/2000 | Heim et al. | |
| 6,106,519 A | 8/2000 | Long et al. | |
| 6,132,427 A | 10/2000 | Jones et al. | |
| 6,169,926 B1 * | 1/2001 | Baker | 607/99 |
| 6,228,081 B1 | 5/2001 | Gobel | |
| 6,235,020 B1 | 5/2001 | Cheng et al. | |
| 6,238,387 B1 | 5/2001 | Miller | |
| 6,241,723 B1 | 6/2001 | Heim et al. | |
| 6,287,305 B1 | 9/2001 | Heim et al. | |
| 6,413,255 B1 | 7/2002 | Stern | |
| 6,533,781 B2 * | 3/2003 | Heim et al. | 606/45 |
| 6,685,704 B2 | 2/2004 | Greep | |
| 6,692,489 B1 | 2/2004 | Heim et al. | |
| 6,758,846 B2 | 7/2004 | Gobel et al. | |
| 2002/0198523 A1 * | 12/2002 | Behl | 606/41 |
| 2003/0109864 A1 | 6/2003 | Greep et al. | |
| 2003/0114848 A1 * | 6/2003 | Cobb | 606/48 |
| 2003/0220638 A1 | 11/2003 | Metzger | |
| 2004/0049180 A1 * | 3/2004 | Sharps et al. | 606/41 |
| 2004/0104455 A1 * | 6/2004 | Shimizu | 257/659 |
| 2004/0116919 A1 | 6/2004 | Heim et al. | |
| 2005/0143725 A1 | 6/2005 | Daners et al. | |
| 2005/0154385 A1 | 7/2005 | Heim et al. | |
| 2005/0234446 A1 * | 10/2005 | Van Wyk et al. | 606/41 |
| 2006/0025757 A1 | 2/2006 | Heim | |
| 2006/0241587 A1 * | 10/2006 | Heim et al. | 606/48 |
| 2006/0241589 A1 * | 10/2006 | Heim et al. | 606/48 |
| 2007/0005054 A1 * | 1/2007 | Heim et al. | 606/41 |
| 2007/0005055 A1 * | 1/2007 | Heim et al. | 606/41 |
| 2007/0005056 A1 * | 1/2007 | Heim et al. | 606/41 |
| 2007/0005057 A1 * | 1/2007 | Heim et al. | 606/41 |
| 2007/0005058 A1 * | 1/2007 | Heim et al. | 606/41 |
| 2007/0005059 A1 * | 1/2007 | Heim et al. | 606/41 |
| 2007/0005060 A1 * | 1/2007 | Heim et al. | 606/41 |

FOREIGN PATENT DOCUMENTS

| | | |
|---|---|---|
| WO | 94/28809 A1 | 12/1994 |
| WO | 96/34571 A1 | 11/1996 |
| WO | 97/11649 A1 | 4/1997 |
| WO | 98/47436 A1 | 4/1998 |
| WO | 9940858 A1 | 8/1999 |
| WO | 02/28301 | 4/2002 |
| WO | 03/090635 | 11/2003 |
| WO | 2005046739 A2 | 5/2005 |
| WO | 2006031289 A2 | 3/2006 |

OTHER PUBLICATIONS

"Coated Electrode Technology . . . ", 2006; ValleyLab, Boulder, Colorado.

"MEGADYNE—Stainless Steel Electrodes"; http://www.megadyne.cor/sstips.hlrn; Jun. 1, 2002; MEGADYNE Medical Products, Inc., Draper, Utah.

English language Abstract of WO 02/28301, Apr. 11, 2002.

PCT/US2005/025681 International Preliminary Report on Patentability and Written Opinion, Feb. 22, 2007.

PCT/US2005/025681 International Search Report and Written Opinion, Jan. 24, 2007.

PCT/US06/25123 International Search Report and Written Opinion, Jan. 25, 2007.

PCT/US06126122 International Search Report and Written Opinion, Jan. 3, 2007.

* cited by examiner

MULTIELECTRODE ELECTROSURGICAL BLADE

This application claims the benefit of priority to U.S. Provisional Application 60/695,692 entitled Multielectrode Electrosurgical Instrument filed Jun. 30, 2005, the entire contents of which are hereby incorporated by reference. This application also claims the benefit of priority as a continuation-in-part to U.S. application Ser. No. 11/185,668, now abandoned, entitled Multielectrode Electrosurgical Instrument filed Jul. 20, 2005, which claims the benefit of priority to U.S. Provisional Application 60/589,508 filed Jul. 20, 2004, the entire contents of both of which are hereby incorporated by reference.

FIELD OF THE INVENTION

The present invention relates to surgical methods and apparatus, and more particularly to applying electrosurgical power to a tissue site to achieve a predetermined surgical effect.

BACKGROUND OF THE INVENTION

The potential applications and recognized advantages of employing electrical energy in surgical procedures continue to increase. In particular, for example, electrosurgical techniques are now being widely employed to provide significant localized surgical advantages in open, laparoscopic, and arthroscopic applications, relative to surgical approaches that use mechanical cutting such as scalpels.

Electrosurgical techniques typically entail the use of a hand-held instrument that contains one or more electrically conductive elements that transfer alternating current electrical power operating at radio frequency (RF) to tissue at the surgical site, a source of RF electrical power, and an electrical return path device, commonly in the form of a return electrode pad attached to the patient away from the surgical site (i.e., a monopolar system configuration) or a return electrode positionable in bodily contact at or immediately adjacent to the surgical site (i.e., a bipolar system configuration). The time-varying voltage produced by the RF electrical power source yields a predetermined electrosurgical effect, such as tissue cutting or coagulation.

During electrosurgical procedures electric current flows through one or more conductive elements, the active electrodes, and transfers electrical current to tissues, often with coincident sparks or arcs of electricity occurring between one or more electrodes and tissues. The overall process causes heating of tissue and the electrode metal. Tissue heating causes tissues to break into fragments or otherwise change into materials that generally differ physically and chemically from the tissue before it was affected by electrosurgery. The tissue changes at the surgical site, such as charring, interfere with normal metabolic processes and, for example, kill tissues that remain at the surface of incisions. The changes in tissues caused by electrosurgical energy, such as killing parts of tissues, are known to interfere with healing at the surgical site.

Beyond damaging tissue at the surgical site, conventional electrosurgery has other drawbacks which limit its applicability or increase the costs and duration of procedures. Induced heating of tissues and electrodes causes smoke plumes to issue from the tissue. Smoke obscures the field of view and hinders surgical procedures and is also a known health hazard. Controlling smoke once it has formed is problematic, requiring the evacuation of large volumes of air in order to capture an appreciable fraction of the smoke with wands that are close to the surgical site where they are in the way, and adds costs in both additional equipment and labor.

The induced heating also generally causes tissue that has been altered by electrosurgery to adhere to and partially coat electrosurgical electrodes. The tissue fragments that adhere to electrodes and coat the electrodes is called "eschar." The coatings on blades that form from tissue and tissue fragments are typically rich in carbon and contain various compounds that tend to make the coatings electrically conductive when energized by the type of power used for electrosurgical procedures. Eschar inhibits the effectiveness of electrosurgical devices and must frequently be removed, hindering surgical procedures.

Despite advances in the field, electrosurgical blades continue to suffer from one or more of the problems of producing smoke, having materials from tissues coat the blades, and damaging tissue. Therefore, a need exists to improve performance in each of these areas. Historically, electrosurgical blades have generally not given consideration to the chemical reaction environment and conditions that occur where the electrosurgical energy interacts with tissue by considering factors such as the propensity of tissue to become trapped in regions that lead to prolonged residence times at reactive conditions that lead to producing smoke and materials that coat blades to form eschar. Likewise, prior art electrosurgical blades did not consider the conductive pathways that can be formed by tissue fragments adhering to blades and the effects that these built-up conductive pathways have on producing smoke, producing more materials that can further coat blades, and the effects that these have during electrosurgery.

SUMMARY

Various embodiments provide a disposable multielectrode electrosurgical blade for use in electrosurgery that controls the environment in which electrosurgical energy transfers to tissue.

The various embodiments of a disposable electrosurgical blade employ blade geometry, blade composition or a combination of blade geometry and composition to reduce or prevent smoke production, eschar accumulations, or tissue damage. The embodiments focus electrosurgical energy to a small amount of tissue for a short duration compared to the amount of tissue and duration than is customary during electrosurgery using conventional technology. Various embodiments yield less eschar accumulation on the electrosurgical instrument by providing an exterior surface of the instrument with a shape that facilitates movement of tissue decomposition products away from the active region of the conductive element. The active region is a region on the conductive element where electrosurgical energy transfers from the blade to tissue. In some embodiments, the tapered configuration includes an electrically conductive element with a tapered section. In some embodiments, the tapered configuration includes configuring an insulating layer with a tapered section. In various embodiments, insulation on the conductive element has a surface free energy that reduces the propensity for electrosurgical decomposition products (defined herein) to stick to the surface. In various embodiments, the shape of the blade minimizes the duration that the active region is near any particular portion of tissue as the blade is moved through tissue as during an incision.

BRIEF DESCRIPTION OF THE DRAWINGS

The accompanying drawings, which are incorporated herein and constitute part of this specification, illustrate embodiments of the invention, and, together with the general description given above and the detailed description given below, serve to explain features of the invention.

DETAILED DESCRIPTION OF THE PREFERRED EMBODIMENT

Figure 1:
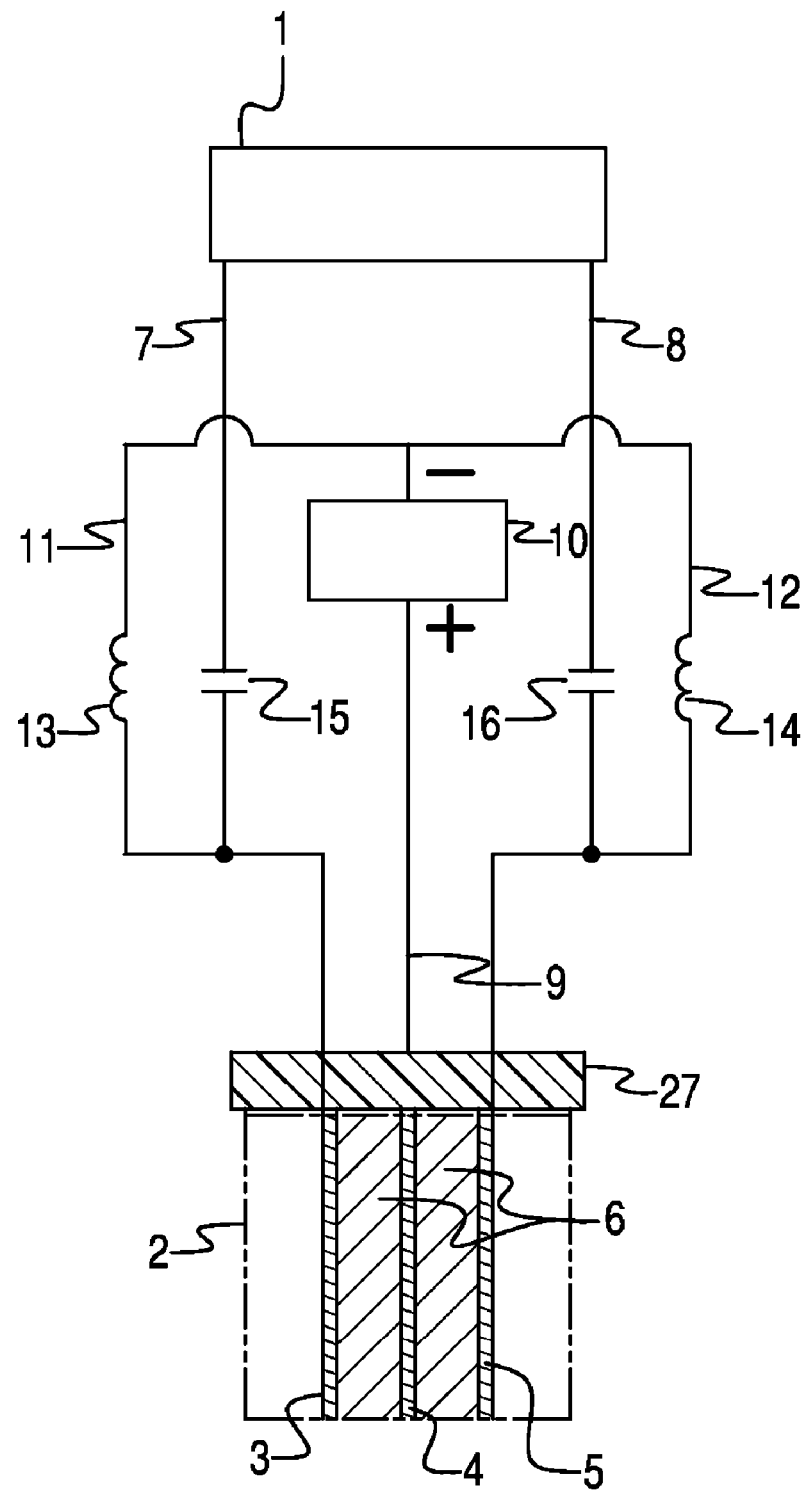
FIG. 1 portrays a system schematic with a general multielectrode blade having active, passive, and return electrodes.

The various embodiments will be described in detail with reference to the accompanying drawings. Wherever possible, the same reference numbers will be used throughout the drawings to refer to the same or like parts.

As used herein, the terms "about" or "approximately" for any numerical values or ranges indicates a suitable dimensional tolerance that allows the part or collection of components to function for its intended purpose as described herein. Also, as used herein, the terms "patient", "tissue" and "subject" refer to any human or animal subject and are not intended to limit the systems or methods to human use, although use of the subject invention on a human patient represents a specific embodiment.

All devices that may be used to produce a predetermined surgical effect by applying RF power to tissue may be referred to herein as electrosurgical "blades" due to their function of partial or complete removal of one or more parts of tissue (including changing the structure such as by at least partially denaturing or decomposing), regardless of their size, shape, or other properties. Use of the term "blade" herein is not intended to restrict the description or any embodiment to a particular shape or configuration. While various embodiments pertain to generally planar elements which may resemble a conventional scalpel blade, other embodiments encompass element configurations which are dissimilar from conventional blades, including, for example, needle, hook and curved configurations.

Reference herein to the purpose and effects of electrosurgical devices as producing "a predetermined surgical effect" encompasses all potential effects generated during electrosurgery. The predetermined surgical effect include, but are not limited to: causing a partial or complete separation of one or more tissue structures or types, including, but not limited to making electrosurgical incisions; cause partial or complete removal of one or more parts of a tissue; changing the structure of tissue, such by at least partially denaturing or decomposing tissue; cutting; hemostasis (such as by inducing coagulation); tissue welding; tissue sealing, and tissue shrinking. Commonly, multiple predetermined surgical effects occur simultaneously, such as cutting and hemostasis both occurring as incisions are made.

Although they may have various forms, all sources of RF power used to power electrosurgical blades will be referred to herein as electrosurgical units and abbreviated by ESU.

The terms "electrode" and "conductive elements" are used interchangeably herein to refer to similar structures without intending to communicate or imply a difference in structure or limitation on any embodiment or claim of the present invention.

Electrosurgical devices come in two common varieties, monopolar and bipolar. Monopolar electrosurgical blades connect to an ESU using a wire while a separate return pad is connected to the ESU by another wire. Bipolar electrosurgical blades connect a set of one or more active electrodes to the ESU with one or more wires and connect another set of one or more return electrodes to the ESU with one or more other wires, wherein the active electrode or electrodes and return electrodes or electrode are connected together so that RF energy may be conveyed through one or more conductive media that contact at least one tissue with such connections between electrodes being either permanent or temporary, such as by being separately inserted into a clamping device or a handle with such connection being fixed or moveable, such as a sliding connection.

The present inventors have recognized that reducing the amount of energy applied to tissue reduces tissue breakdown and that the amount of applied energy can be reduced by reducing the exposure to electrosurgical power (where electrosurgical power is the rate at which electrosurgical energy is applied) either by reducing the power level, the time of exposure to electrosurgical power, or by reducing both the power level and the time of exposure. Various embodiments reduce the energy to which tissue is exposed by proper selection of blade geometry, blade materials, and the amount of power used.

More generally in this regard, energy discharge from electrosurgical instruments may be in the form of electrical energy and/or thermal energy. Electrical energy is transferred whenever the electrical resistance of a region between an electrosurgical instrument and tissue can be broken down by the voltage of the electrosurgical power. Thermal energy is transferred when thermal energy that has accumulated in the electrosurgical instrument overcomes the thermal resistance between the instrument and the tissue (i.e. due to temperature differences therebetween) and is transferred to tissue by conduction, radiation and/or convection. Transferring electrosurgical energy to tissue occurs at portions of the electrosurgical instrument which cause the desired surgical effect, such as forming an incision. Such portions of the instrument are called functional areas. All other portions of the electrosurgical instrument are nonfunctional, and transfer of electrosurgical energy to tissue from these portions should be minimized. Electrosurgical energy may be transferred to tissue without direct contact with the functional area by means of electrical sparks and radiative and convective heat transfer. As used herein, the term "contact" relating to the position of blades or electrodes near tissue encompasses both actual contact and positioning of a functional area close enough to tissue for transfer of electrosurgical energy to occur.

Pyrolysis is the breakdown of molecules into smaller moieties by the action of heat (physical fragmentation), typically followed by subsequent recombination of these thermal fragments to form larger species. As used herein, the term "electropyrolysis" refers to the process whereby electrical energy in the form of sparks or arcs interacts with tissue to break down tissue constituents by heat, electron interactions with materials, photon interactions with materials, or any combination of these.

In general terms, electrosurgery is the process by which high voltage (e.g., voltages greater than about 100 volts) electrical power is applied to tissue to achieve a predetermined surgical effect. Such voltages are typically employed as high frequency (e.g., frequencies greater than about 5 kHz) and most commonly use frequencies greater than about 100 kHz to reduce neuromuscular stimulation. The energy is transferred to tissue at the surgical site using one or more electrodes. Electrical energy is transferred as well as thermal energy which comes from electrodes becoming hot as electrical power moves through them, producing $I^2R$ power losses which manifest themselves as heat, some of which is transferred to tissue via conduction, radiation, and convection. As used herein, the term "electrosurgical energy" refers to all of the energy transferred to tissue during electrosurgery, regardless of form or transfer mechanism, and including both electrical and thermal energy.

Without restriction to any particular theory of operation regarding its form or method of use, the following descriptions of processes during electrosurgery are provided to illustrate one or more candidate processes that could be present during electrosurgery to facilitate subsequent descriptions of the various embodiments.

Tissue breaks down where sparks or hot metal contact it. This breakdown of tissue is believed to be caused by rapid heating of tissue where electrosurgical energy, principally electrical sparks and thermal energy from hot metal, contacts tissue and electropyrolysis and hydrolysis lyse tissue constituents.

During electrosurgery a variety of reaction products are produced. Electropyrolysis is believed to be a cause of tissue breakdown during electrosurgery. One result of electropyrolysis during electrosurgery is the production of hot water and steam which promote hydrolysis of tissues. For example, electropyrolysis and hydrolysis are believed to break down proteins and produce a range of products, including cyclic and linear polypeptide materials. Electropyrolysis is also believed to be the process by which electrosurgery is able to cut or otherwise break down tissues that have a cellular structure (e.g., muscle tissue) as well as tissues that do not have a cellular structure (e.g., collagen fibrils in ligaments).

Beyond electropyrolysis products, other electrosurgery products are also formed. Most notable are changes in state in which materials change their state (e.g., steam forming when water changes from liquid to gas) but are otherwise not changed chemically. During electrosurgery some products have altered structure, but otherwise retain their chemical identity, such as when proteins denature and then refold into shapes different from those prior to denaturation. During electrosurgery some products retain their chemical structure and state, but change physically in other ways (e.g., air being heated so that its specific volume increases).

Finally, some electrosurgery processes can cause materials, such as cellular contents or viral particles, to be liberated or moved with a stream of other materials, such as being conveyed by flowing steam or hot air produced during electrosurgery.

Collectively, all of the materials produced or altered during electrosurgery, including those from electropyrolysis, change of state, change of structure, change of volume, and liberation are referred to herein as the "products of electrosurgery," "electrosurgical decomposition products," or "electrosurgical products". The collection of processes that break down or alter tissues during electrosurgery are referred to here as electrosurgical tissue decomposition processes.

Some of the resulting materials form smoke or steam and some of the resulting materials form substances that stick to blades. When electrosurgery is performed in a gaseous environment, such as air or carbon dioxide, particularly when incisions are made, a common result using conventional technology is a smoke plume. The smoke plume is believed to consist primarily of pyrolysis and electropyrolysis products, including steam and hot air along with materials such as cellular contents and other entrained materials.

When electrosurgery is performed, including when incisions are made, some of the products of electrosurgery form deposits on electrodes contacting or in close proximity to tissue. These deposits, called eschar, are believed to begin forming when sticky materials, such as denatured proteins, adhere to electrode surfaces. Other materials may also be mixed in with the sticky materials. As electrosurgery proceeds, thermal energy continues to pyrolyze these materials on the electrodes leading to the production of substances having a higher carbon:hydrogen content than the starting materials. Some resulting materials conduct electricity at the voltages used, perhaps due to the presence of ions from salts or by having high carbon contents, and form an electrically conductive coating on the blade, even if the blades surface is coated with an insulating coating. Therefore, eschar formation on the outside of an insulated electrode that has, for example, only an edge exposed, can have an electrically active area that extends from the exposed edge because of conductive eschar deposits forming on the blade's surface and being in electrical contact with the exposed edge. This conductive deposit can expose more tissue to prolonged exposure to electrical energy.

Prior to the present invention, bipolar blades suffered from the requirement that the electrodes be close enough together so that current would reliably pass into tissue but not be so close together as to allow short circuiting to occur though a bridge of conducting material, such as carbonaceous material formed from thermally decomposed tissue products. Such deposits of thermally decomposed tissue products are called eschar. Eschar readily forms in the high temperature environment local to electrosurgical blades. When electrodes are placed far enough apart to prevent short circuiting by eschar it becomes difficult to ensure that both active and return electrodes contact tissue. When the electrodes are close enough to ensure that both active and return electrodes contact tissue the rapid formation of short circuiting bridges ensues.

Prior art for bipolar electrosurgery blades have replaced the return pad with one or more electrodes on the blade itself. The additional electrode(s) are connected to the ESU using a wire. The electrical path is generally described as coming from the ESU, to one electrode on the blade, through patient tissue, into the other electrode on the blade, and then back to the ESU. All of the prior art for bipolar blades has two or more electrodes, all of which are connected to the ESU such that they all experience the same voltage differences with such voltage differences either being direct current or alternating current and never a combination of the two types of electrical energy. For example, U.S. Pat. No. 164,184 for a bipolar electrosurgical device describes using a pair of conductors spirally wound onto a rubber probe body in which the conductors are embedded. The device is not used to make incisions and uses direct current supplied from a battery to apply the same voltage difference to all electrodes. A bipolar electrosurgical device described in U.S. Pat. No. 1,983,669 has a pair of conductors twisted around an insulator that is powered by high frequency (i.e., alternating current) energy. U.S. Pat. No. 4,011,872 shows an electrosurgical device featuring two, three or four electrodes all connected to the same radio frequency energy source by a single conductor.

The electrodes may take on a variety of configurations, as described using the following exemplary prior art. In U.S. Pat. No. 3,970,088, U.S. Pat. No. 3,987,795, and U.S. Pat. No. 4,043,342, (collectively "the Morrison patents"), electrode configurations are disclosed wherein the surface areas of the active and return electrodes are substantially different. The Morrison patents disclose using a porous material surrounding electrodes to enhance stable startup. The Morrison patents further disclose using multiple electrodes in which all of the electrodes are connected to the ESU such that the RF power is applied to all of the electrodes. U.S. Pat. No. 4,202,337 and U.S. Pat. No. 4,228,800 disclose bipolar blade configurations with split electrodes in which all of the electrodes are connected to the ESU such that RF power is applied to all of the electrodes. The '337 and '800 patents further disclose bipolar blades that insert into a handle that has electrical contacts that provide electrical connections to the ESU such that a pair of side electrodes are shorted together and act as the return electrode with a center electrode acting as the active electrode. U.S. Pat. No. 4,232,676 discloses pairs of electrodes in which the voltage applied may be either direct current or alternating current but in either case the voltage difference applied between all of the electrodes is the same. U.S. Pat. No. 4,706,667 discloses a pair of return electrodes flanking a cutting electrode. U.S. Patent Application Publication No. 20030130658 discloses multiple electrodes having dissimilar materials in which RF power is applied to all of the electrodes.

The present inventors have recognized that applying a direct current between the electrodes of a bipolar electrosurgical blade reduces or prevents the formation of short circuits, even when the electrodes in blades are close together. The present inventors have further recognized that the propensity for such short circuiting to occur can be reduced by limiting the amount of exposed electrode surface area. The present inventors have yet further recognized that such application of direct current between electrodes and limiting of electrode surface areas are mutually beneficial and complement each other.

When conventional bipolar blades are used, eschar tends to start to form on one electrode or another. The deposit then grows in thickness as it propagates from that electrode, increasing the electrical impedance at that electrode from what it would be absent the eschar deposit. As the eschar deposit grows it can span the gap between active and return electrodes in bipolar devices, leading to a short circuit current path for the RF power that reduces or prevents power transfer to tissue, thus interfering with or preventing the desired surgical effect from occurring.

In short, the present inventors have recognized that a means is needed to prevent the formation or accumulation of the short circuits from materials formed by electrosurgical tissue decomposition processes. The various embodiments comprise an electrosurgical instrument that includes a multiplicity of electrodes with at least one active and at least one return electrode. In a system context, the electrodes of the electrosurgical instrument have not only alternating current flowing but also direct current flowing between at least one active electrode or at least one return electrode and another electrode. Such direct current reduces or prevents the formation and accumulation of electrosurgical tissue decomposition products on electrodes. The mechanisms by which direct current reduces or prevents eschar accumulation are not precisely known but are believed to include effects caused by electrolysis of water and shifts in chemical reactions. Electrodes having a more negative voltage are believed to accumulate small amounts of hydrogen in a layer believed to restrict eschar accumulation. The negative charge is also believed to inhibit dehydrogenation reactions that would otherwise occur at the temperatures that exist during electrosurgery, thus inhibiting the formation of at least some of the carbon-rich constituents that comprise eschar.

The method of reducing eschar on bipolar blade electrodes by applying direct current may be applied when other means are employed to reduce unnecessary/undesired electrical discharge during electrosurgical procedures. Such reduction(s) reduce the amount of direct current required to reduce or prevent eschar accumulations and are achieved via enhanced localization of electrical power transmission to a tissue site. More particularly, the various embodiments markedly reduce electrical discharge from both functional and nonfunctional areas of an electrosurgical instrument by insulating either or both functional and nonfunctional areas. The amount of direct current required to reduce or prevent eschar accumulation is reduced when one or more means are employed to reduce the local heating that promotes eschar formation. Such means for reducing local heating include providing for an effective level of heat removal away from functional portions of an electrosurgical instrument and/or by otherwise enhancing the localized delivery of an electrosurgical signal to a tissue site such as by reducing the exposed areas of either or both functional and nonfunctional areas by using thermal insulation.

Various embodiments of the present invention comprise an electrosurgical instrument that includes a multiplicity of electrodes for carrying electrosurgical power in which the electrodes are electrically isolated from each other and provide for being connected to an ESU in an overall system such that at least one active electrode and at least one return electrode exist, thus forming at least one set of bipolar electrodes. In an embodiment, direct current voltage may be applied across this pair of electrodes to reduce or prevent formation of electrosurgical tissue decomposition products (ETDPs) such as eschar. The electrode with the negative DC voltage will have little or no accumulation of ETDPs. However, the electrode with the positive DC voltage will tend to accumulate ETDPs. Various embodiments include at least one electrode in the system that is not directly connected to the RF power coming from the ESU. An electrode not powered by the ESU does not directly produce the predetermined surgical effect and any such electrodes are called passive electrodes herein. All passive electrodes are connected to one pole of a DC power source and the bipolar electrodes are connected to the other pole of the DC power source. In use, the passive electrodes would be connected to the positive pole and the bipolar electrodes would be connected to the negative pole of the DC power source. Therefore, both of the bipolar electrodes are connected to RF power, which produces the predetermined surgical effect and tends to produce ETDPs, and to a DC power source, while the passive electrodes are connected only to DC. In an embodiment system configuration, the negative DC on the bipolar electrodes prevents or reduces accumulations of ETDPs and the absence of RF power on the passive electrodes prevents or reduces accumulations of ETDPs on them.

In an embodiment of an electrosurgical instrument designed to make incisions, there would be one pair of bipolar electrodes and one passive electrode. The regions near bipolar electrodes have temperatures that tend to promote eschar formation, but the negative DC current inhibits or prevents eschar accumulation. The passive electrodes are not powered by the ESU so the regions around them do not have the conditions that promote eschar formation.

In an electrosurgical instrument used to produce an electrosurgical effect on tissue in an environment where the electrodes are surrounded by a medium that provides electrical communication between at least one of the bipolar electrodes and tissue, an example of such a medium being an electrically conductive liquid containing substantial amounts of water, one or more pairs of bipolar electrodes may be employed, with or without the presence of one or more passive electrodes. In this second instance the bipolar electrodes of the system would have RF power applied to them that has a voltage bias that leads to a nonzero root mean square (RMS) voltage that is adequate to electrolyze water local to the electrodes. When one or more passive electrodes are used the connections to DC power would be as previously described and electrolysis would also occur. The electrolysis of water produces at least a partial covering of gas bubbles around enough electrodes to create a sufficient impedance between the bipolar electrodes for an ESU to supply power adequate to produce the desired electrosurgical effect.

When one or more passive electrodes are used the bipolar electrodes are both connected to the same pole of a DC power source. To prevent this common connection from shorting the active and return electrodes one or more electronic AC blocking components that allow DC current to flow while inhibiting passage of alternating current are put in series with the connections from the DC power source to the bipolar electrodes. In an embodiment, the components would be inductors sized to produce substantial impedance, such as over about 500 ohms, to the RF power produced by the ESU while producing acceptably small DC resistance, such as less than about 100 ohms. The direct current voltage difference between one or more passive electrodes and one or more of the bipolar electrodes needs to be adequate to at least inhibit eschar accumulation while not producing too much electrolysis, such as by being at least about 0.5 volts and less than about 100 volts. Relatedly, insulating material may be interposed and interconnected between at least the two bipolar alternating current electrodes to define an electrosurgical blade. Such electrical insulating material preferably has a dielectric withstand strength of at least 50 volts and may comprise either a single layer or multiple layers with one or more other electrodes interposed between insulation layers.

In an embodiment, three electrodes that are substantially colinear over at least one dimension are used with at least part of the electrodes oriented parallel to each other with all of the electrodes separated from and physically interconnected to the other electrodes by one or more electrical insulating materials to define an electrosurgical blade. The electrosurgical blade may be configured so that at least part of each electrode may contact tissue or an electrically conductive substance in contact with tissue, with two of the electrodes being bipolar electrodes with an alternative current voltage applied to them and the remaining electrode having a direct current voltage difference between it and the bipolar electrodes.

In various embodiments, an outer insulating layer made of one or more materials selected to reduce thermal/electrical discharge from non-functional portions of the electrodes may be provided to surround at least a portion of the bipolar electrodes, such as the active and return electrodes. In various embodiments, an outer insulating layer having a thermal conductance of about 1.2 W/cm$^{2\circ}$ K and a dielectric withstand strength of at least about 50 volts may be employed. Such insulating layer may advantageously comprise one or more materials with pores that have been sealed with a sealing material so as to prevent biological materials from entering the pores. In an embodiment, such sealing material may contain one or more of various silicate materials or materials that form silicates. In an embodiment, at least part of the outer insulating layer or the substance bonding at least one pair of electrodes comprise one or more materials that include a colloidal silicate material and may further comprise one or more hydrolyzable materials that in combination form a thermally insulative substance that by itself is essentially hydrophobic and does not allow biologic material to penetrate its surface.

In various embodiments, one or more of the electrodes are metal with the electrodes provided to have a thermal conductivity of at least about 0.35 W/cm ° K, and may advantageously comprise a metal selected from the group: gold, silver, aluminum, copper, tantalum, tungsten, columbium, and molybdenum, and alloys thereof. In various embodiments, one or more of the electrodes may be coated or plated with a substance or element that imparts resistance to oxidation such as a plating of gold or silver.

In various embodiments, the blade includes at least three conductive layers or electrodes, including an intermediate layer or electrode that defines a peripheral edge portion of reduced cross-section (e.g., about 0.001 inches thick or less) for electrosurgical power or direct current power transmission. Such intermediate layer or electrode may comprise a metal having a melting point of at least about 2600° F.

Heat sink structures may be included in various embodiments to establish a thermal gradient away from functional portions of the instrument (i.e., by removing heat from the electrodes). In an embodiment, the heat sink structures may comprise a phase change material that changes from a first phase to a second phase upon absorption of thermal energy from the electrodes.

In various embodiments, an electrosurgical blade is provided in which the electrodes are spaced apart using one or more types of electrically insulating particles, such as polymeric, glass, or ceramic beads, that have maximum cross dimensions approximately equal to the distance desired for spacing the electrodes from each other. In this regard, the spacing particles may be included as part of the above-noted electrical insulating material provided between the electrodes. In turn, the particles may be at least partially in contact with at least one additional material of the electrical insulating material that bonds to the electrodes of the electrosurgical blade.

Various embodiments include a multielectrode electrosurgical instrument and related system and method that employ structures for reducing or preventing eschar accumulations on or between electrodes by a means other than the spacing between electrodes, geometry of electrodes, or composition of electrodes. Such structures for reducing or preventing eschar accumulations on or between electrodes may require or be augmented by electrode spacing, geometry, or composition. Various embodiments apply to instruments in which at least one pair of electrically isolated electrodes are mechanically connected such that their spacing is limited to a predetermined range (such range possibly being a fixed distance) and electrically connected to an ESU such that RF current will flow between the electrodes when they contact an electrically conductive medium such as tissue or an electrically conductive liquid or vapor. These electrodes are bipolar electrodes and any device having one or more sets of bipolar electrodes is a bipolar instrument. All bipolar instruments, regardless of their intended purpose, design, shape, geometry, configuration, materials, or other aspects are referred to as electrosurgical blades.

Various embodiments of the structures for reducing or preventing eschar accumulations on or between bipolar electrodes involve having direct current flow through at least one of the bipolar electrodes with at least part of the current flow passing through tissue or passing through at least one electrically conductive medium in electrical communication with at least one of the electrodes. In one embodiment the direct current flows between both of the electrodes of a pair bipolar electrodes with at least part of the current flowing through tissue or passing through at least one electrically conductive medium in electrical communication with at least one of the electrodes. Some embodiments have at least one pair of bipolar electrodes and for at least one passive electrode (an electrode not powered by an ESU) and are configured and operated so direct current flows between said passive electrode and at least one of the bipolar electrodes with said direct current at least in part flowing through tissue or passing through at least one electrically conductive medium in electrical communication with at least one of the electrodes.

Bipolar or passive electrodes may be any shape or shapes such as, but not limited to, being substantially flat, having one or more curves, being shaped as closed curves such as rings or hoops, being shaped as nonclosed curves such as semicircles or crescents, being planar, being nonplanar such as curved spatulas, having bends or curves such as hooks, encompassing volumes such as cups or cylindrical volumes, being substantially blunt, having one or more regions that taper from one thickness to a lesser thickness, being solid such as spheres or balls, having opposing faces such as forceps or scissors, and having one or more openings such as holes, meshes, pores, or coils.

FIG. 1 illustrates an embodiment in which a passive electrode is used. ESU 1 supplies power to multielectrode blade 2. Multielectrode blade 2 consists of one or more active electrodes 3, one or more passive electrodes 4, one or more return electrodes 5, with the electrodes insulated from each other by interior insulation 6. Recognize that ESU 1 supplies alternating current power so that the flow of electric current between active electrodes 3 and return electrodes 4 periodically reverses as the voltage output of ESU 1 changes. Multielectrode blade 2 may be without insulation other than that separating the electrodes or additional insulation may surround the electrodes. These aspects of the invention are described later.

Active electrodes 3 may be one or more electrically conductive elements and whenever referred to in the singular case are understood to also include the use of a multiplicity of electrodes connected electrically to have substantially the same power source or power sources. Similarly, passive electrodes 4 may be one or more electrically conductive elements and whenever referred to in the singular case are understood to also include the use of a multiplicity of electrodes connected electrically to have substantially the same power source or power sources. Also similarly, return electrodes 5 may be one or more electrically conductive elements and whenever referred to in the singular case are understood to also include the use of a multiplicity of electrodes connected electrically to have substantially the same power source or power sources.

Power from ESU 1 to multielectrode blade 2 is conveyed via supply conductive element 7, which can be preferably an insulated metal conductor for at least part of its length and terminates into handle 27 that holds the multielectrode blade 2 in a manner that conveys power to the active electrode 3 and that is convenient for having the multielectrode blade 2 contact patient tissues. The electrical circuit for power from the ESU 1 to multielectrode blade 2 is completed via return conductive element 8, which can be an insulated metal conductor for at least part of its length and which terminates into the handle 27 that holds multielectrode blade 2 in a manner that conveys power from return electrode 5 to the return conductive element 8.

Passive electrode 4 is powered by the passive conductive element 9, which can be an insulated metal conductor for at least part of its length that terminates into the handle 27 that holds the multielectrode blade 2 in a manner that conveys power to the passive electrode 3.

DC power supply 10 supplies power to passive electrode 4 via passive conductive element 9, preferably with the positive DC voltage being supplied to passive electrode 4. DC power supply 10 provides power to active electrode 4 via DC conductive element 11. DC power supply 10 provides power to return electrode 6 via DC conductive element 12.

One or more RF current impedance elements 13 and 14 may be in DC conductive elements 11 and 12 so that supply conductive element 7 and return conductive element 8 are kept substantially isolated from each other and short circuit and to substantially isolate passive electrode 4 and DC power supply 10 from being in RF current paths parallel to supply conductive element 7 or return conductive element 8. RF current impedance elements 13 and 14 can be inductive elements providing at least about 500 ohms impedance at the output frequency of ESU 1 and preferably providing at least about 1000 ohms impedance at the output frequency of ESU 1 and more preferably providing at least about 5000 ohms impedance at the output frequency of ESU 1. RF current impedance elements 13 and 14 can be are at least about 50 microhenries and preferably at least about 1000 microhenries and more preferably about 10,000 microhenries. RF current impedance elements 13 and 14 need to convey DC power and can be capable of carrying at least about 5 milliamperes and preferably at least 50 milliamperes and preferably have a DC resistance of less than about 100 ohms and more preferably of less than about 50 ohms and still more preferably less than about 20 ohms.

DC power supply 10 can provides voltage in the range of about 0.5 volt to 100 volts and preferably in the range of about 2.5 volts to 50 volts and more preferably in the range of about 5 volts to 20 volts. DC power supply 10 can provide current in the range of about 0.0100 milliamperes to 1 ampere, preferably in the range of about 10 milliamperes to about 0.1 ampere.

ESU 1 is isolated from DC power by the presence of one or more DC blocking elements 15 and 16. DC blocking elements can be capacitors having a low equivalent series resistance (ESR) at the frequency of the power from ESU 1 and having an impedance of less than about 500 ohms preferably less than about 100 ohms and more preferably less than about 50 ohms and more preferably of less than about 10 ohms at the output frequency of ESU 1. In some embodiments, DC blocking element 15 may be omitted and DC current flow blocked by DC blocking element 16.

Figure 2:
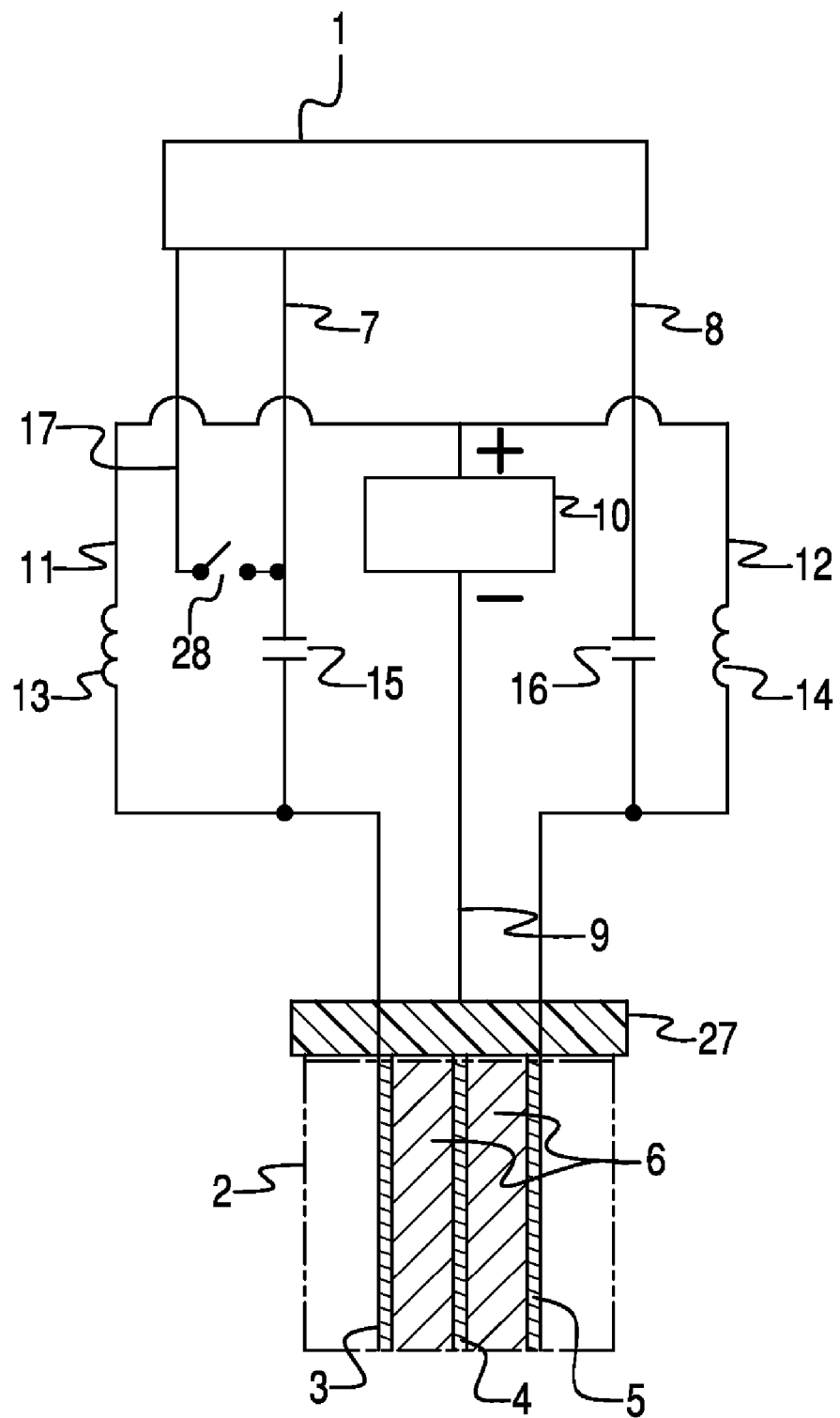
FIG. 2 portrays a system schematic with a general multielectrode blade having active, passive, and return electrodes with an activation switch.

Users can control when ESUs supply power by using either a footswitch or a switch in a handle that holds blades. When the switch is in the handle it is common for one or more signal wires to come from the ESU to the handle and for the supply conductive element 7 to be part of the signal path. As is known to those skilled in the art of ESU design, the RF power supply and the signal path are isolated and separated in the ESU and commonly the control signal is a DC signal that uses the supply conductive element 7. To not interfere with this control strategy the DC blocking element 15 can be located to not prevent the control signal from reaching ESU 1. FIG. 2 illustrates the same schematic as FIG. 1 with the addition of control signal conductive element 17 and control switch 18. In an embodiment, control signal conductive element 17 and control switch 28 are in the handle 27, although they are not shown that way in FIG. 2. DC blocking element 15 can be placed so that it is not in series with control switch 28 and ESU 1. In an embodiment, DC blocking element 15 is located in handle 27.

DC power supply 10 may take on any form that provides the proper voltage and current. In one embodiment it may be one or more batteries. In another embodiment it may be an external power supply powered from a power cord connected to AC line power from a wall outlet or power from a connection in ESU 1. An embodiment obtains DC power from the RF power supplied by ESU 1. In an embodiment DC power supply 10 contains one or more active components, such as diodes or other rectifying elements, and is connected to the RF output of ESU 1 and converts part of the RF output from ESU 1 into DC power.

Figure 3:
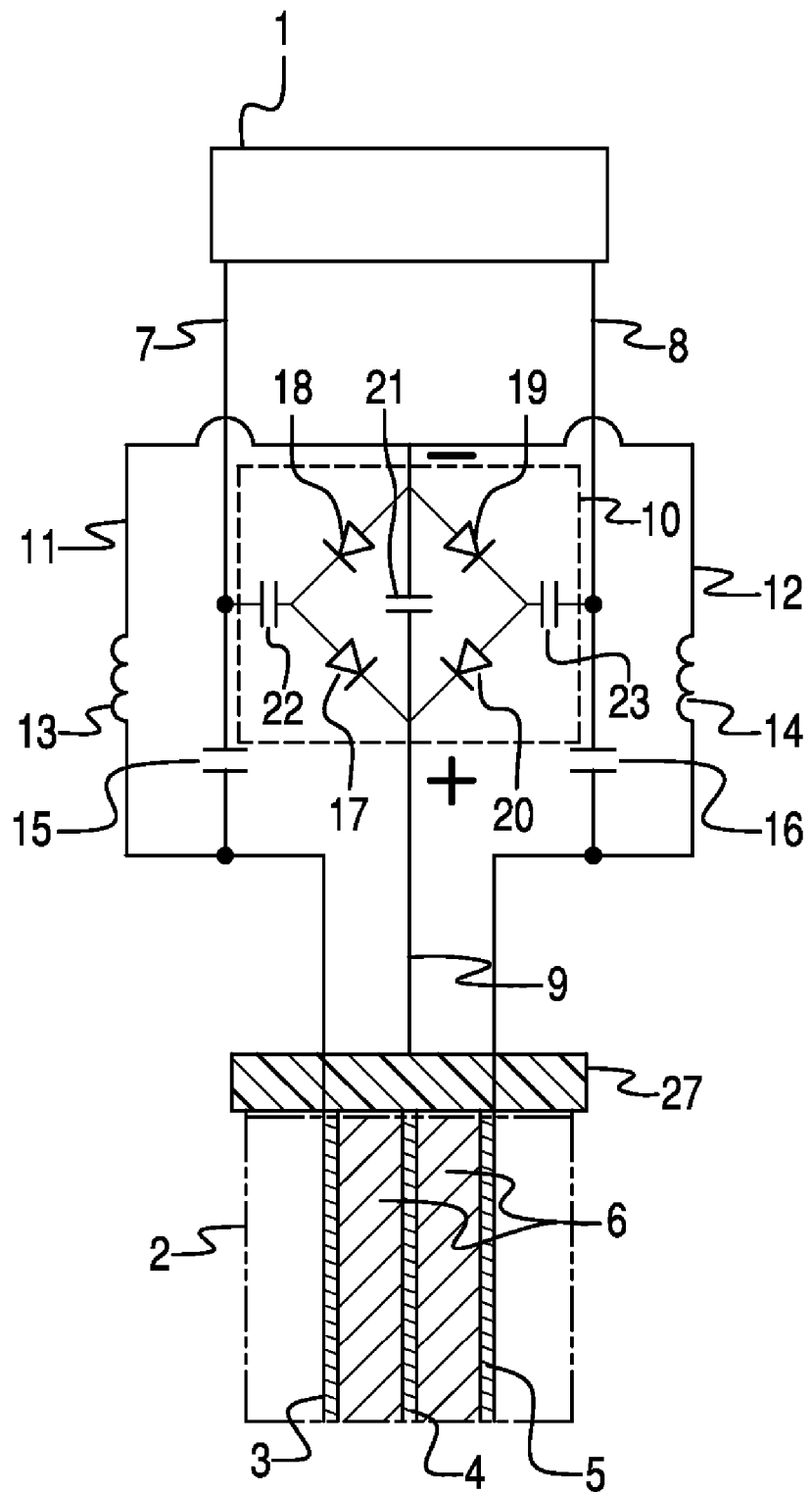
FIG. 3 portrays a system schematic with a multielectrode blade having active, passive, and return electrodes with DC power derived from the RF power.

FIG. 3 illustrates a bridge circuit that produces DC power from the RF power supplied by ESU 1. DC power supply 10 contains four rectifying elements, 17, 18, 19, and 20, configured in a bridge configuration. A voltage control system 21 controls the output voltage. Voltage control system 21 is illustrated as a capacitor but may consist of one or more active elements to further control voltage. The voltage control system may consist of a capacitor to reduce the magnitude of the voltage deviations. In an embodiment, the voltage control system includes a means for controlling the maximum output voltage, such as by using a zener diode in series with a resistive load. One or more RF voltage reduction elements, 22 and 23, are used to drop the voltage output by ESU 1 to produce a DC output voltage in the range desired. The presence of one or more RF voltage reduction elements, 22 and 23, reduces the power dissipation requirements that may be imposed on voltage control system 21. Rectifying elements, 17, 18, 19, and 20 can be diodes and may be of any type that has a reverse recovery time compatible with frequencies of at least 20 kHz and preferably of at least 100 kHz and even more preferably of at least 200 kHz and still more preferably of at least 500 kHz to be compatible with most of the ESUs being used, and finally compatible with at least 2 MHz to be compatible with almost all ESUs being used. Rectifying elements, 17, 18, 19, and 20 need to withstand the voltages output by the ESU and the RF voltage reduction elements, 22 and 23 allow the use of a range of diodes, such as Schottky diodes, that can withstand preferably at least 500 volts and more preferably at least 1000 volts.

In various embodiments, one or more of the elements of DC power supply 10, RF current impedance elements 13 and 14, and DC blocking elements 15 and 16 may be incorporated into the ESU 1, incorporated into an adapter that connects to ESU 1, incorporated into plugs and connectors used to connect supply conductive element 7 and return conductive element 8 to ESU 1 (these plugs and connectors are not shown in FIG. 1, 2, or 3), or may be incorporated into the handle 27.

In use, connections are made to ESUs with a plug that connects supply conductive element 7 to a power supply connector on the ESU and with another plug that connects return conductive element 8 with a return connector on the ESU. In an embodiment, the elements of DC power supply 10, RF current impedance elements 13 and 14, and at least one of the DC blocking elements 15 or 16 are housed in a plug that connects the supply conductive element 7 to the ESU and that has a wire that passes from it to a plug that connects to a return connector on the ESU. In another embodiment, the elements of DC power supply 10, RF current impedance elements 13 and 14, and at least one of the DC blocking elements 15 or 16 are housed in the handle 27 which holds the blade. Such embodiments may either be reusable or may be a single use sterile disposable.

FIGS. 1, 2, and 3 illustrate the passive electrode being between the active and return electrodes. This arrangement is not required. Passive electrodes may be anywhere that allows them to be in electrical communication with the active electrodes. Passive electrodes do not need to be mechanically connected to the device of which the active and passive electrodes are a part. For example, one or more passive electrodes could attach to the patient in the form of one or more electrode pads and connect to DC power supply 10 using a wire. The passive electrodes can be mechanically connected to the device of which the active and passive electrodes are a part.

The electrodes may be any shape, size, or arrangement that leads to a configuration and composition suitable for a particular application. For example, an arthroscopic ablation instrument used in a submerged electrically conductive liquid may be configured with multiple active and return electrodes with suitable shapes, such as in the form of linear or curved edges or pins, close together at the end of a shaft and a single passive electrode could be spaced back away from end of the shaft and be in the form of a ring around the shaft. All of the electrodes would be surrounded by electrically conductive liquid and, thus, be in electrical communication with the liquid. In another arrangement, a split ring that forms a bipolar pair could have inlaid a passive electrode.

Figure 4:
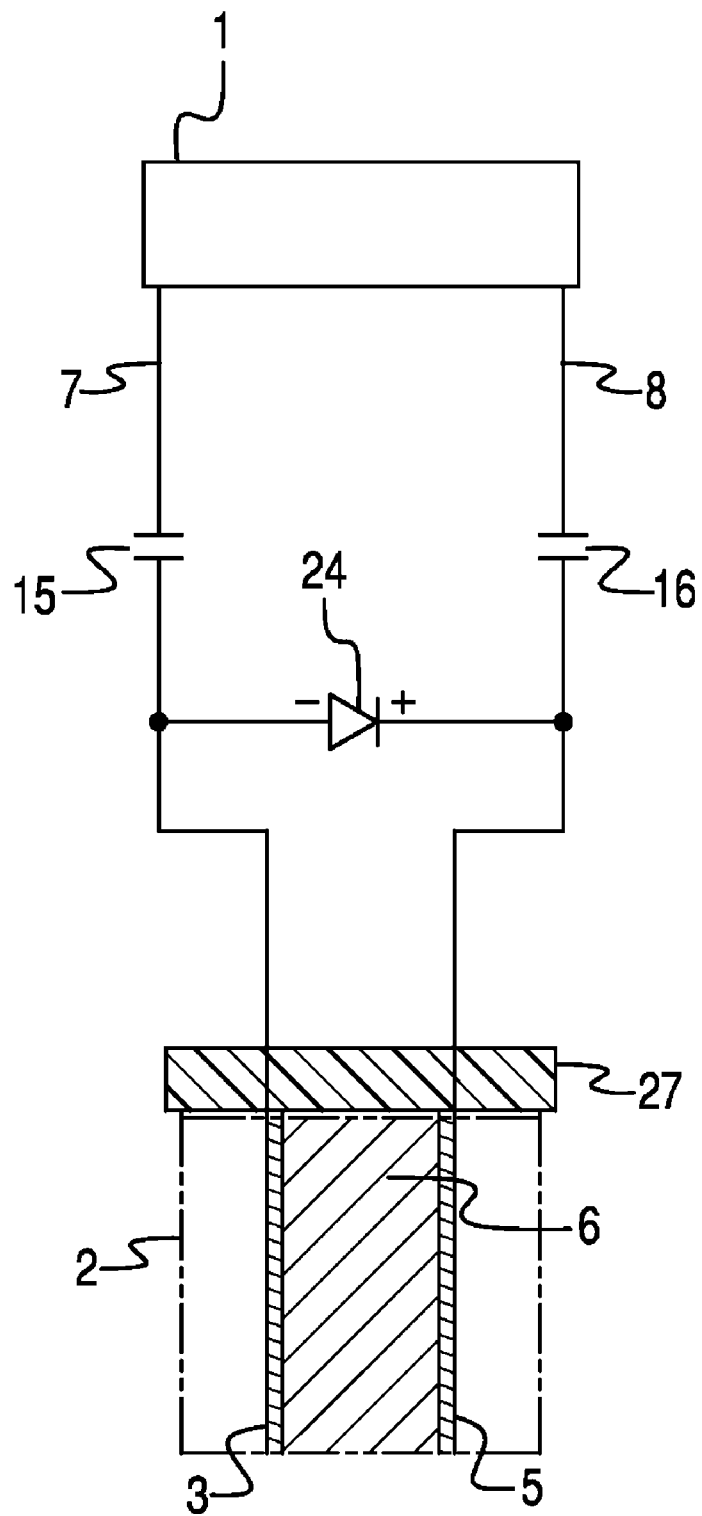
FIG. 4 portrays a system schematic with a multielectrode blade having active and return electrodes with DC power derived from the RF power.

FIG. 4 illustrates an embodiment that uses fewer components than those illustrated in FIGS. 1-3. Direct current is supplied directly between active electrode 3 and return electrode 5. No passive electrode is used. Any direct current power source may be used when direct current is supplied directly between the bipolar electrodes. An embodiment uses RF power supplied by the ESU and one or more rectifying elements. FIG. 4 illustrates using rectifying element 24 to produce a DC voltage. Contrary to common design practice for rectifiers such as diodes, rectifying element 24 can have a reverse recovery time less than the period of the AC power supplied. Preferably the reverse recovery time of rectifying element 24 is between about 0.05 and 0.5 the period of the AC power supplied and more preferably is between about 0.1 and 0.25 the period of the AC power supplied. Using such reverse recovery times leads to substantial reverse current flow through the rectifying diode before it starts to inhibit backwards current flow. This slow response leads to a substantially lower direct current voltage being applied across active electrode 3 and return electrode 4 than would otherwise occur using common design practice. Preferably, diodes rated as standard or fast recovery can be used. Preferably, diodes with a voltage withstand of at least 300 volts and more preferably at least 1000 volts may be used.

Figure 5:
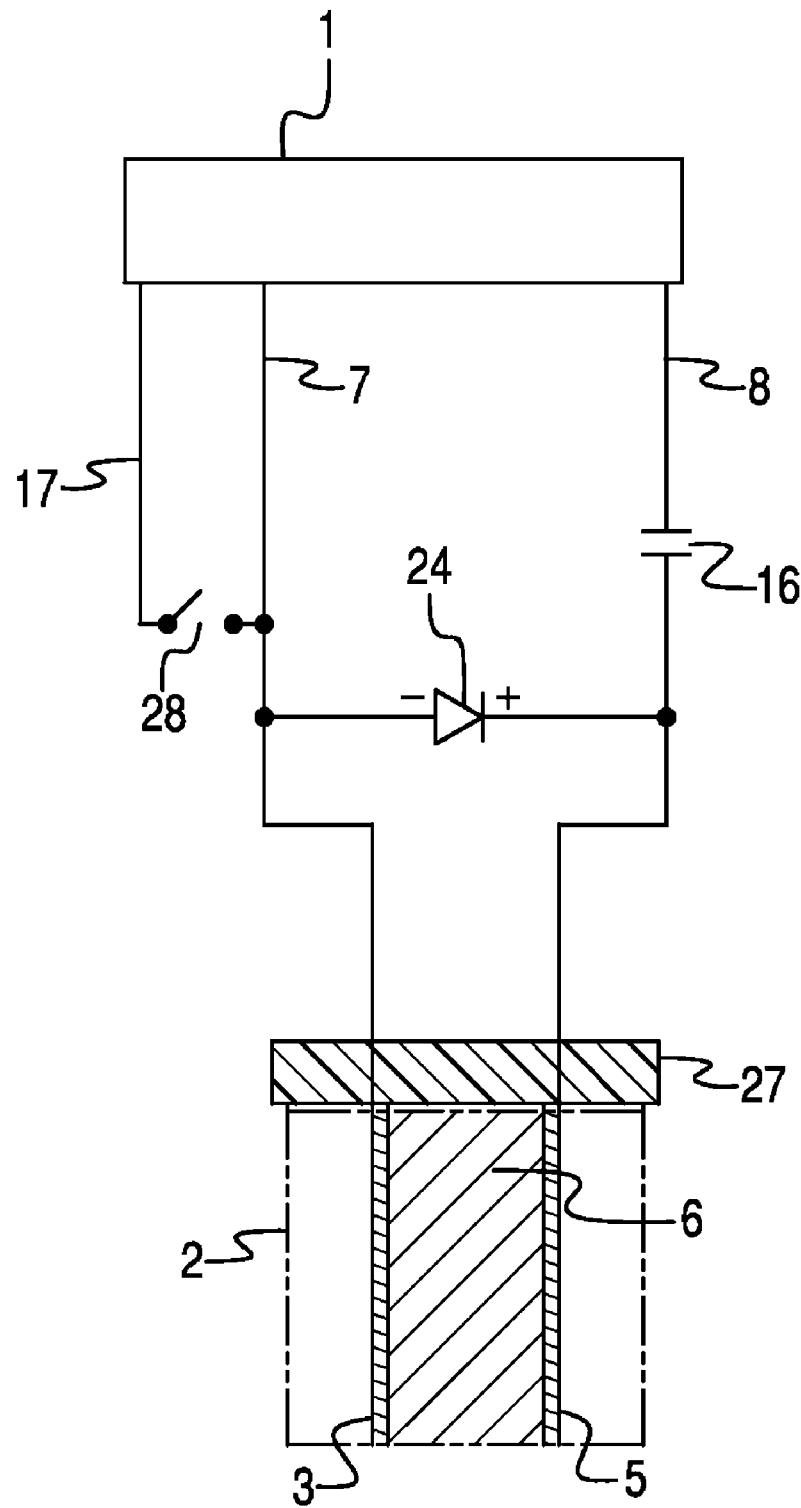
FIG. 5 portrays a system schematic with a multielectrode blade having active and return electrodes with DC power derived from the RF power with an activation switch.

DC blocking element 15 can interfere with passage of control signals that may need to pass between one or more switches in handle 27 and ESU 1. FIG. 5 illustrates an embodiment that does not include a DC blocking element in the supply conductive element 7. Control signal conductive element 17 and control switch 28 are illustrated to show that control switch 28 can be located anywhere. In an embodiment, the control switch 28 is located in handle 27.

In configurations without passive electrodes the electrodes may be any shape, size, or arrangement that leads to an arrangement suitable for a particular application. For example, an arthroscopic ablation instrument used in a submerged electrically conductive liquid may be configured with multiple active and return electrodes with suitable shapes, such as in the form of linear or curved edges or pins, close together at the end of a shaft. All of the electrodes would be surrounded by electrically conductive liquid and, thus, be in electrical communication with the liquid. In another arrangement, a split ring that forms a bipolar pair could have inlaid a passive electrode.

Alternatives to the illustrated embodiments exist. For example, the embodiments of FIG. 4 or 5 would tend to keep eschar from accumulating on active electrode 3 but not offer the same level of protection to return electrode 5. A passive electrode with a separate DC supply could be included that would cause DC current to pass between the passive electrode and the return electrode and reduce or prevent eschar accumulations on return electrode 5.

ESU 1 may have multiple RF supplies connected via a multiplicity supply of and return conductive elements to a multiplicity of active and return electrodes that are not electrically connected and thus operating substantially independently of each other to provide multiple voltage waveforms, possibly with phase angles, frequencies, and voltages that differ from one another. DC power supply 10 may have multiple direct current power sources connected via a multiplicity of passive supply conductive elements to a multiplicity of passive electrodes or to a multiplicity of active or return electrodes that are isolated from one another from DC current supply.

Passive electrodes need to be close enough to the bipolar electrodes to allow DC current to flow between the passive electrodes and the bipolar electrodes. The passive electrodes may contact patient tissue within six feet of the bipolar electrodes. In some embodiments, the passive electrodes may contact patient tissue within six inches of the bipolar electrodes. In some embodiments, the passive electrodes may contact patient tissue within one inch of the bipolar electrodes. For many blades, such as those embodiments used for incisions, the passive electrodes may be within about 0.5 inches of the bipolar electrodes, and in some embodiments within about 0.1 inches of the bipolar electrodes, and in other embodiments within 0.010 inches of the bipolar electrodes. The closer spacing between the passive electrodes and the bipolar electrodes reduces the overall size of the instruments and reduces the amount of tissue through with which DC current passes.

Figure 6:
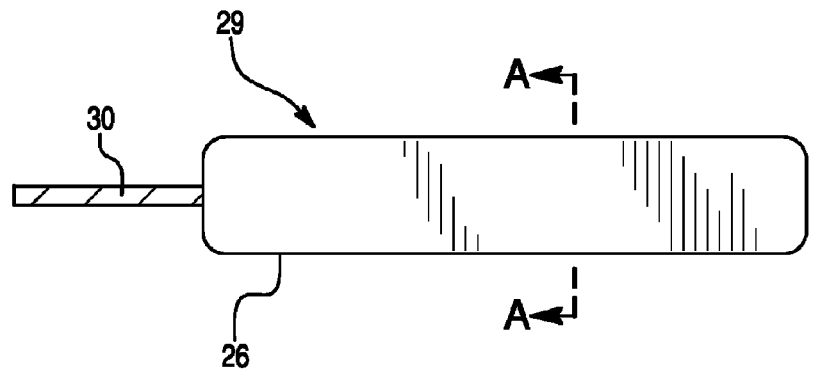
FIG. 6 illustrates a side view of an electrosurgical instrument having an electrode blade.

FIG. 6 illustrates an electrosurgical instrument configuration with blade 29 connected to shaft 30. Shaft 30 typically connects to a handle (not shown) and typically provides means in the form of one or more conductors for conveying electrical power to blade 29. The blade 29 includes a functional portion, or contact face 26 (e.g. a cutting edge), for contacting patient tissue. FIGS. 7, 8, 9, and 11 are cross sections of blade 29 in FIG. 6 when viewed through cross section AA.

FIGS. 7, 8, 9, 10, and 11 illustrate various example embodiment configurations of multielectrode blades. To reduce DC current flow various embodiments limit the amount of exposed electrodes surface area by extending interior insulation 6 over all of the interior surfaces of the electrodes except for the functional surfaces. To further reduce DC current flow an embodiment employs outside insulation 25 to limit the electrode surface area exposed on the outside of the blades. These configurations show passive electrode 4 between active electrode 3 and return electrode 5. As described earlier, this arrangement is not required. However, when this configuration embodiment is used, insulation between the nonfunctional surfaces of active electrodes 3 and return electrodes 5 can be included. If, for example, the active electrode is between the passive and return electrodes, the outer surface of the passive electrode does need to be insulated to reduce DC current flow when only the functional areas of active and return electrodes already have limited surface areas exposed.

Figure 7:
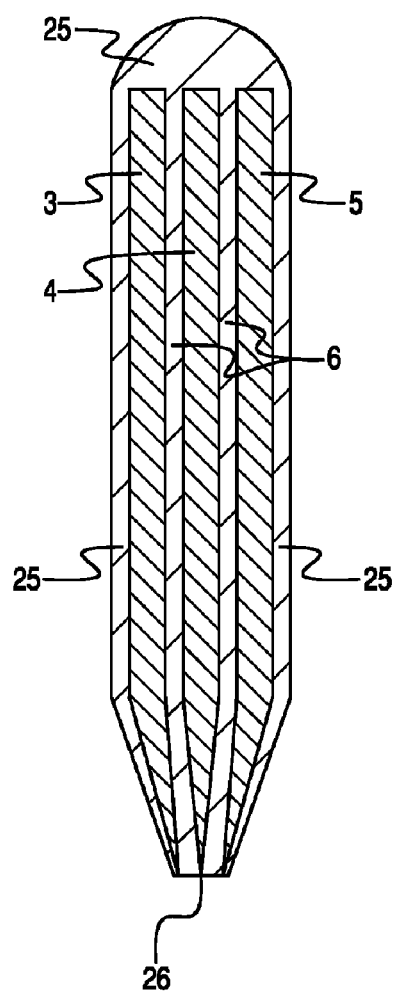
FIG. 7 portrays a cross section of a multielectrode blade having active, passive, and return electrodes with a substantially flat contact face.

FIG. 7 illustrates a configuration in which the electrodes taper to fine edges and the blade is shaped to present a substantially flat contact face 26 where only the sharp edges of the electrodes are exposed through the surface of the interior insulation 6 and outside insulation 25. FIG. 7 illustrates only one active electrode 3 and one return electrode 5, however multiple active and return electrodes could extend out in an alternating arrangement. Such arrangements would increase the size of the flat contact face 26 through which the electrodes emerge. These multiple electrode arrangements can be used for applications where large surface areas are to undergo electrosurgical treatment, such as in arthroscopic tissue ablation procedures. For these applications an embodiment has the electrodes emerging from the surface to form a rough surface that also mechanically abrades the surface of the tissue as it penetrates the tissue. For these applications the electrodes may protrude between about 0.0001 and about 0.5 inches and in an embodiment, the electrodes protrude between about 0.001 and about 0.1 inches. For such applications a single passive electrode can be used and in an embodiment, the passive electrode can be located away from the region where the active and return electrodes are located to maximize the amount of surgical effect caused by the active and return electrode in a give surface area. The passive electrode can be attached to the shaft of the instrument within about 0.5 inches of the location of the active and return electrodes and no restriction exists regarding minimum spacing between the passive electrode on the shaft and active or return electrodes on the working surface where the surgical effects occur.

Figure 8:
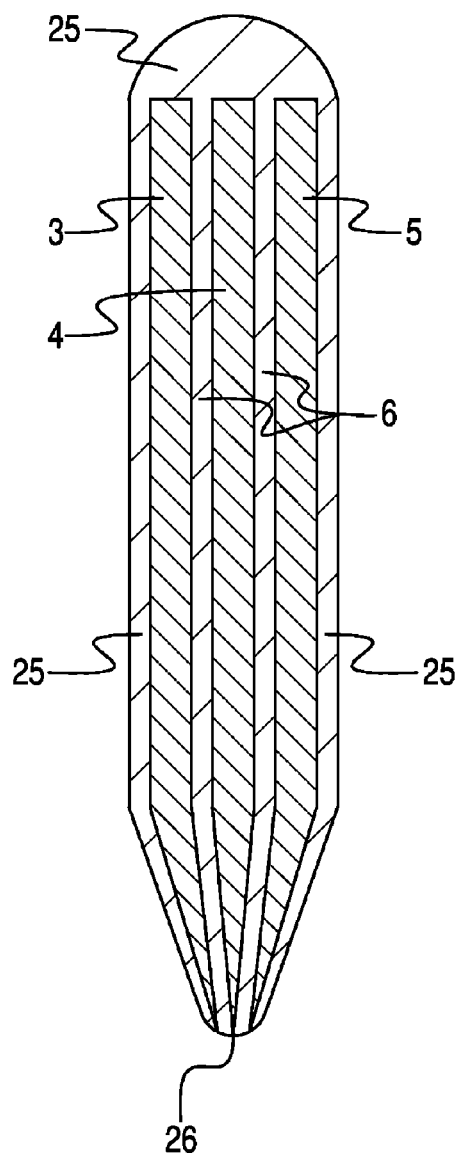
FIG. 8 portrays a cross section of a multielectrode blade having active, passive, and return electrodes with a convex contact face.

For making incisions it is preferable for the width of the blade contacting tissue to be small to reduce drag. For making incisions it is further preferred to have small surface areas for functional areas and to also have small surface areas for nonfunctional areas near active and return electrodes to reduce the total exposed surface area where electrosurgical effects occur. Having small surface areas reduces the time that tissue is exposed to conditions that cause ETDPs and also reduces the residence time of ETDPs in the hot regions near the active and return electrodes. Long residence times tend to promote tissue decomposition and the ensuing formation of smoke, eschar, and collateral tissue damage. The preferred small exposed surface areas where electrosurgical effects occur reduce the formation of smoke, eschar, and tissue damage. Various embodiments for blades used for incisions taper a portion of the blade by tapering at least the outside insulation 25, as shown in FIG. 7 such that the narrowest part of the blade is the contact face 26 where the functional areas are located, which is the same areas where active electrode 3 and return electrode 5 are exposed. FIG. 8 illustrates an embodiment in which the electrodes 3, 4 and 5, and insulation 6 and 25 are shaped to form a constantly curving strictly convex surface at the functional contact face 26. The strictly convex profile reduces the residence time of material in regions where smoke, eschar, and tissue damage occurs. FIG. 8 also illustrates an embodiment in which electrodes are shaped to further taper the blade in order to reduce residence time. The strictly convex shape in the functional regions where the electrodes are exposed can be achieved without shaping the blades to accentuate the taper.

Figure 11:
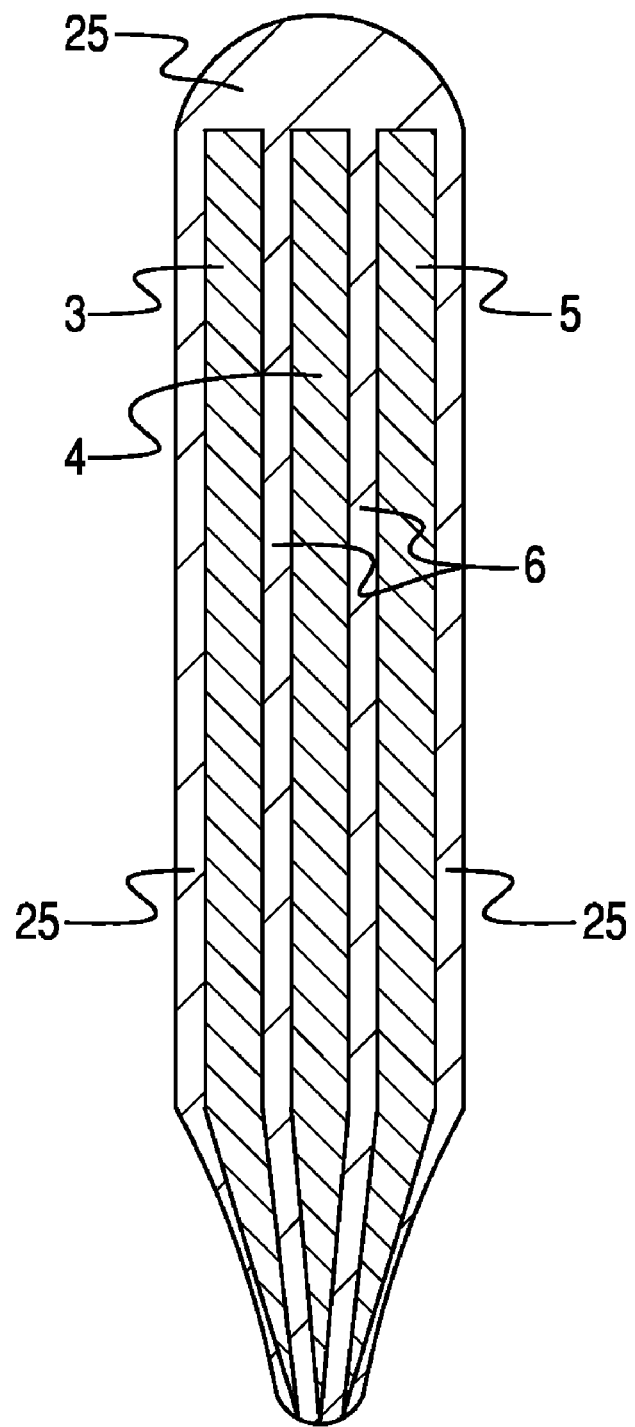
FIG. 11 portrays a cross section of a multielectrode blade having active, passive, and return electrodes with a convex contact face having electrode edges exposed and an adjacent concave surface.

In various embodiments, the tapered blade portion where the blade tapers toward the contact face 26 can be concave while keeping the contact face 26 where the electrodes are exposed strictly convex. FIG. 11 illustrates an embodiment that has a concave surface where the blade tapers and is convex where the electrodes are exposed. The strictly convex contact face 26 can be used where the electrodes contact the tissue and between the electrodes. The portions of the blades outside of the electrodes can be tapered so that they are either flat or concave, as illustrated in FIG. 11.

For blades used for making incisions it is preferable for the blades to be thinner than about 0.5 inches and more preferable for them to be thinner than about 0.05 inches. When blades are too thick they impede the incision process and drag through the tissue. Metal electrodes preferably thinner than about 0.2 inches and more preferably thinner than about 0.1 inches and still more preferably thinner than about 0.02 inches should be used to produce blades with the desired thinness. Insulation thickness on the outside of the bipolar electrodes and the total insulation thickness between bipolar electrodes preferably thinner than about 0.2 inches and more preferably thinner than about 0.1 inches and still more preferably thinner than that about 0.02 inches should be used to produce blades with the desired thinness. The spacing between electrodes can be between about 0.001 and 0.2 inches, preferably between about 0.002 and 0.100 inches and more preferably between about 0.005 and 0.015 inches.

Figure 9:
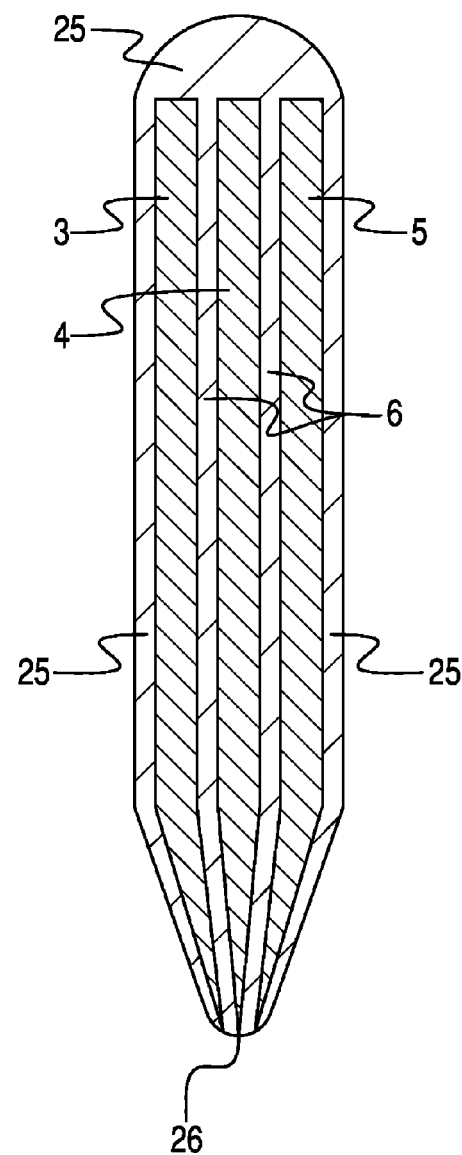
FIG. 9 portrays a cross section of a multielectrode blade having active, passive, and return electrodes with a convex contact face with electrode edges exposed.
Figure 10:
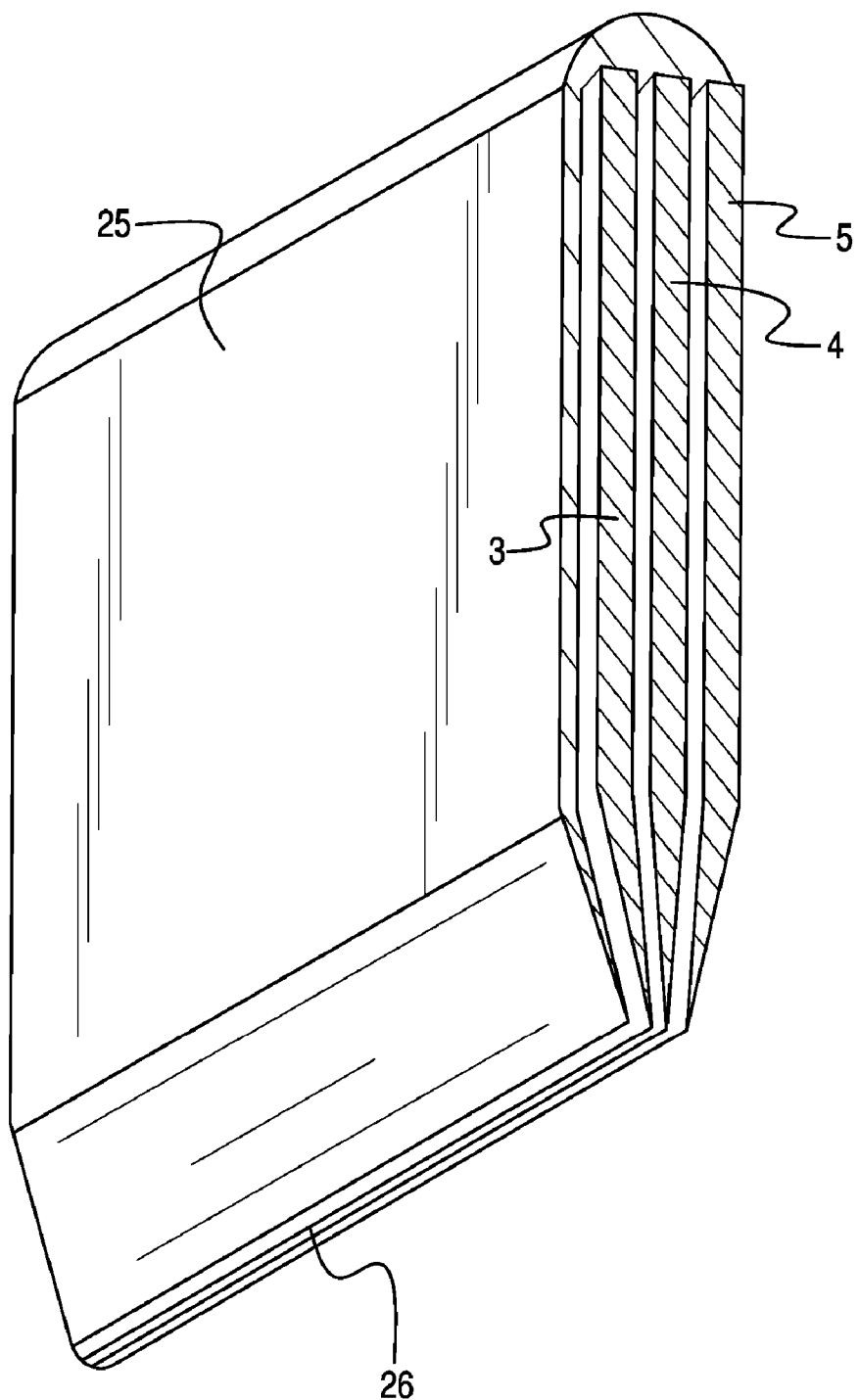
FIG. 10 portrays a perspective view of a portion of a multielectrode blade with insulation cut away to show active, passive, and return electrodes tapered to a convex contact face having electrode edges exposed.

FIG. 9 and FIG. 10 illustrate a blade in which slightly more electrode metal than the very edge is exposed through the insulation. FIG. 10 illustrates an elongated blade in which the active electrode 3, passive electrode 4, and return electrode 5 extend along a dimension to form approximately coplanar surfaces and, consequently, has a contact face 26 in the form of a cutting edge that is substantially longer than it is wide. Such configurations may be suitable for blades used to make incisions. Illustrated is a configuration in which the cutting edge of contact face 26 is approximately a straight line. The cutting edge could have other shapes, for example having one or more parts that have shapes that approximate part of an ellipse or circle instead of approximately a straight line.

If part of the edge is behind or covered by insulation then electrosurgical energy transfer is inhibited and accomplishing the corresponding desired predetermined electrosurgical effect is hindered. To provide reasonable manufacturing tolerance and not have part of the edges of electrodes exposed more than an extremely fine edge needs to be exposed. More than 90 percent of the active and return electrode edges along the functional surfaces can be exposed, preferrably more than 95 percent of the active and return electrode edges be exposed along the functional surfaces, and more preferrably more than 99 percent of the active and return electrode edges be exposed along the functional surfaces. Furthermore, it is preferable to limit the DC current flow and residence time of tissues at the conditions that cause smoke, eschar, and tissue damage. The smallest dimensions (the widths) of the edges of the active and return electrodes can be smaller than about 0.020 inches, preferably that the widths of the edges of the active and return electrodes are smaller than about 0.005 inches and more preferable that the widths of the edges of the active and return electrodes are smaller than about 0.001 inches and still more preferable that the widths of the edges of the active and return electrodes are between about 0.00001 and 0.001 inches.

FIG. 11 illustrates the active electrode 3, passive electrode 4, and return electrode 5 emerging from the insulation of a blade. This arrangement in which electrodes have at least one region exposed without insulation can be employed in various embodiments for either connecting blades to handles or to have blades connect to other features, such as shafts, that will become part of a final device. The exposed regions of the electrodes can vary and the lengths of the blades can be stepped or otherwise made unique to facilitate producing electrical contact surfaces.

From an overall system standpoint, the DC power source could be part of the ESU or may be external to the ESU. When external to the ESU the DC power source could be an adapter connected to the ESU to which a surgical instrument is connected or the DC power source could be a part of the surgical instrument. The DC power source could be self contained, such as a battery, could obtain power from an outside source, such as an AC wall outlet, or it could obtain its power from the RF power supplied to the instrument by the ESU. When obtaining power from the RF power supplied by the ESU one or more rectifying components such as diodes would be used. Typically one or more electronic components, such as capacitors, would be used to isolate the ESU from the DC power being added to the RF power supplied to the instrument while still allowing RF power to be conveyed to the instrument.

Which electrodes are active, return, and passive may be fixed and unchanging or the polarities of the electrodes may change during use. Changing polarities during use may facilitate procedures such as making incisions by reducing the amount of force required to move a blade through tissue. Switches would be used to change the connections of the electrodes to active, return, and DC power poles. Typically, such switches would use one or more electronic semiconductor components such as bipolar transistors, field effect transistors, or insulated gate bipolar transistors. The switching can be facilitated by timing the transition from one polarity setting to another during those times when the RF voltage applied to the blade is substantially less than the peak voltages applied by the ESU. Such low voltage switching would include switching during the times when voltages are close to zero, such as commonly occur with ESU outputs having crest factors greater than about 1.5, and commonly are greater than 2 or when ESU outputs have duty cycles less than 100% and commonly less than 75 percent.

Closely spaced electrodes may be made by placing a thin coat of an insulating material that bonds to electrode material on an individual electrode element and then placing another electrode element on the insulating bonding material. The bonding material needs to produce a surface with dielectric strength suitable for withstanding the voltage difference across the electrodes. Suitable materials include polydiorganosiloxanes, silicone elastomers, fluorosilicones, and polytetrafluoroethylenes. Other approaches include laminating a solid polymer sheet between electrode elements and interposing layers of adhesive. Additional approaches include using ceramic material that bonds the electrodes, including formulating the ceramic with particles or fibers with dimensions that space the electrodes apart to facilitate maintaining desired electrode spacing and planarity. An embodiment uses a ceramic material to bond the electrodes such that the bonding material extends between the electrodes to the exposed surfaces of the electrodes. An acceptable ceramic material to use for bonding is one of the outer insulating materials described below. Another embodiment uses one of the insulating materials described below that includes one or more hydrolyzable silanes including those that have halogens and even more preferable is to use one of the insulating materials described below that contain one or more hydrolyzable silanes that contain fluorine. In another embodiment, high temperature polymer materials may be used to bond the electrodes.

In an embodiment, the bonding material used between electrodes may have added to it particles that are not electrically conductive that will space the electrodes apart when the electrodes are pressed together or otherwise fixtured during manufacturing. Examples of such particles are glass beads or fibers, ceramic beads or fibers, or polymeric beads or fibers. Such particles can be generally rigid and capable of withstanding temperatures greater than about 200° F. without deforming under load, such as glass or ceramic beads or fibers. Also, such spacing particles individually have approximately uniform dimensions such as being spherical. The spacing particles can comprise a range of dimensions, but in general the largest size particles will be the ones that hold the electrodes apart when they are pressed together or otherwise fixtured. The maximum diameter of the largest particles, or equivalent dimension that determines the spacing of the electrodes, can be between about 0.001 and about 0.2 inches, and more preferably between about 0.002 and 0.100 inches and even more preferably between about 0.005 and about 0.015 inches.

The amount of electrosurgical products produced depends upon the amount of energy applied to tissue, the rate at which the energy is applied, and the length of time that tissue is exposed to sources of the energy. While conventional electrosurgical systems have attempted to control these factors by means of ESU settings, the present inventors have recognized that the configuration of electrosurgical blades also affect the time and amount of energy applied to portions of tissue, and thus to the generation of electrosurgical products. For example rough blade functional surfaces tend to retain tissue fragments and thus expose such tissue fragments to electrosurgical energy for longer durations than occurs when the blade has smooth functional surfaces. If recesses or pockets exist where material can be held in place in close proximity to the functional surfaces, the residence time for chemical reactions to occur increases for trapped materials. With increased residence time, more lysis occurs, leading to increased smoke and eschar production. As low molecular weight materials are lysed from trapped materials they leave as smoke and gases that are relatively rich in hydrogen, leaving behind an increasingly carbon-rich material. This material is eschar. When deposited on the surface of an insulating layer it effectively widens the electrically conductive edge, which exposes more tissue to electrosurgical energy and increases the time at which tissue is exposed to lysing conditions. Exposing more tissue to lysing conditions and exposing tissue for longer periods to such conditions causes more smoke and eschar to form, and thus it is desirable to prevent or reduce the occurrence of such conditions.

Using cutting as an example electrosurgical process, the power settings typically used during electrosurgery employing conventional electrosurgical systems are over 30 Watts, and often are on the order of 40 to 100 Watts. Theoretically, the amount of power required for cutting is much lower, between about 2 and about 15 Watts. The surplus power beyond that theoretically required drives unwanted reactions such as the production of smoke and eschar as well as overheating tissue that kills cells.

Figure 15:
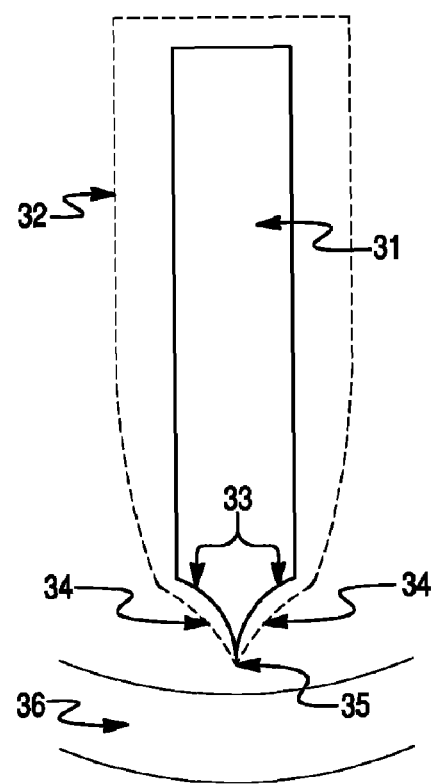
FIG. 15 portrays a cross-section of a blade with a conductive element that has a concave taper that has been insulated whereby the outer taper to the edge is not defined by a single smooth curve at the conductor edge.
Figure 16:
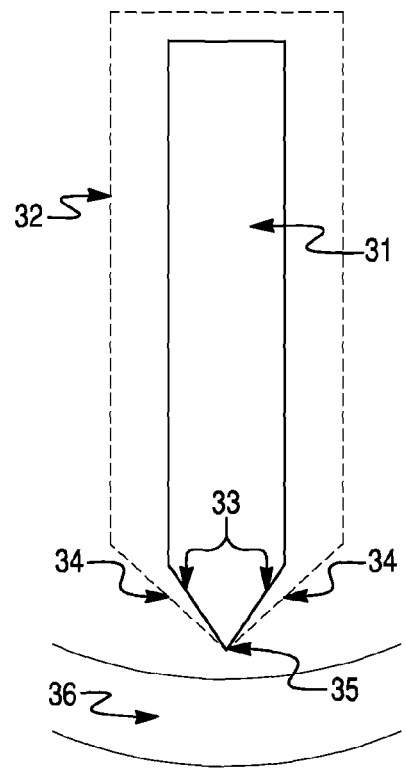
FIG. 16 portrays a cross-section of a blade with a conductive element that has a substantially flat taper that has been insulated whereby the outer taper to the edge is not defined by a single smooth curve at the conductor edge.

The various embodiments employ blade geometry, blade composition or a combination of blade geometry and composition to reduce or prevent smoke production, eschar accumulations, or tissue damage. The embodiments focus electrosurgical energy to a small amount of tissue for a short duration compared to the amount of tissue and duration than is customary during electrosurgery using conventional technology. In the embodiments, the electrosurgical energy flows from a conductive elements that is surrounded by insulation except for an exposed edge or point. Providing a relatively small exposed edge or point on the conductive elements restricts RF energy flow to this portion of the conductive element, minimizing energy transfer from the rest of the conductive elements which is covered by insulation. In some embodiments, the exposed edge on the conductive elements can be formed by tapering down the insulation covering from its thickness at the wide part of the conductive element to minimal thickness adjacent to the exposed edge, as illustrated in FIGS. 15 and 16. In other embodiments, the conductive elements geometry ends in a point that is not covered by insulation, as also illustrated in FIGS. 15 and 16.

Various embodiments comprise electrosurgical instruments that use blade shape and composition to reduce the production of smoke and eschar by, among other methods, reducing the time that materials are exposed to electrosurgical energy. The result is reduced smoke production, reduced eschar production, and reduced tissue damage.

Various embodiments include electrosurgical instrument features that promotes the free flow of electrosurgical decomposition products such as steam, gases, and vapors away from regions near the functional surfaces where electrosurgical energy interacts with tissue and such gaseous decomposition products form. It is believed that facilitating the flow of gaseous decomposition products away from the functional surfaces where they are generated reduces the local gas pressure in the vicinity of the functional surfaces which would otherwise rise with the buildup of gaseous products. By reducing the pressure and promoting the flow of electrosurgical decomposition products, the conditions which cause pyrolysis and electropyrolysis of tissue and electrosurgical products are reduced, particularly in the vicinity of the functional surface just removed from where the desired electrosurgical effect occurs. It is believed that continued pyrolysis and electropyrolysis of electrosurgical decomposition products leads to more generation of smoke and eschar. Thus, by reducing pressure, and thus temperatures, in the vicinity of the functional surfaces and facilitating the escape of electrosurgical decomposition products, generation of smoke and eschar can be substantially reduced.

Figure 12:
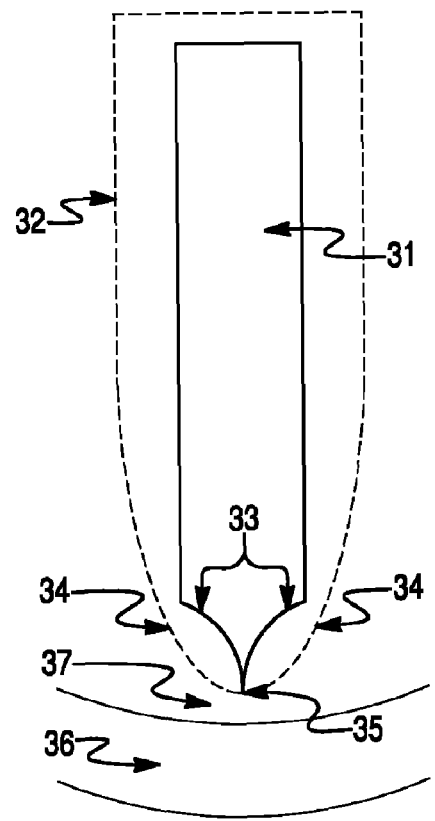
FIG. 12 portrays a cross-section of a blade that has been insulated whereby the outer taper to the edge is defined by a single smooth curve at the conductor edge.
Figure 13:
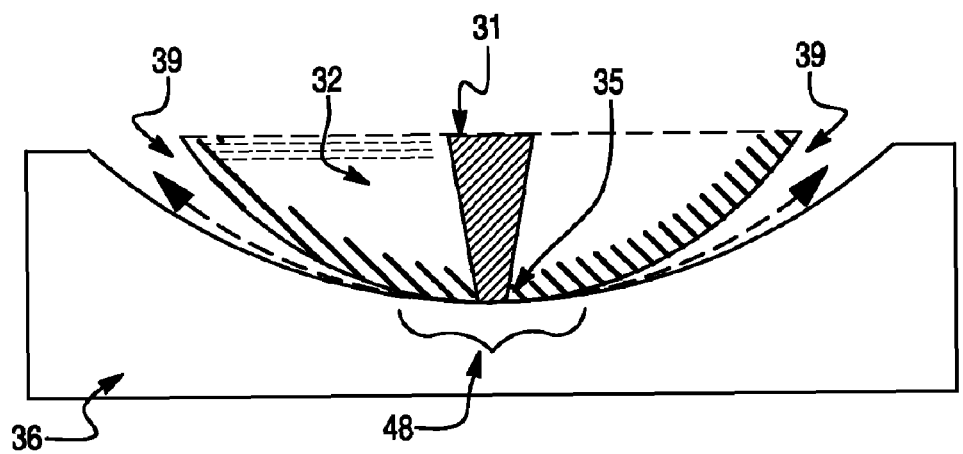
FIG. 13 portrays a magnified section of the region where electrosurgical energy interacts with tissue for the blade illustrated in FIG. 1.

In various embodiments, the electrosurgical instrument or blade features a narrow surface, edge or point in the vicinity of the functional area that reduces the length of the path that gases or vapors must traverse from the point of generation to reach ambient conditions, thus the distance and time during which decomposition products are exposed to high temperatures. In such embodiments, examples of which are illustrated in FIGS. 15-20, the functional surface is an edge of the blade that has at least one dimension (such as thickness) which is less than the corresponding dimension (such as thickness) of nonfunctional surfaces. In various embodiments, the edge or point is comprised of a metal conductor that is surrounded by insulation except for a section where the metal is exposed. In such embodiments, the outer profile of the insulation where the metal conductor is exposed is thinner than the outer profile at a distance removed from the exposed surface. In an embodiment, the edge or point is shaped so that it forms an acute angle where it comes in close contact with tissue during use. This aspect of the embodiments reduces the local gas pressure compared to, for example, a blade that has a relatively flat surface shape adjacent to the functional surface, such as when the combination of the insulation and conductive elements form a round or parabolic profile, such as illustrated in FIGS. 12 and 13. In some embodiments, the edge is formed by tapering the profile so that the radial dimension at the functional surface is less than the radius of part of the nonfunctional surface of the blade.

Figure 21:
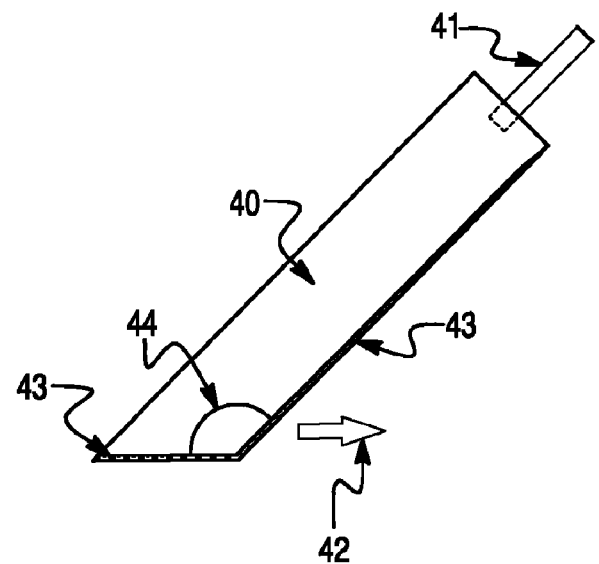
FIG. 21 portrays a side view of a blade with two exposed edges at an obtuse angle.
Figure 22:
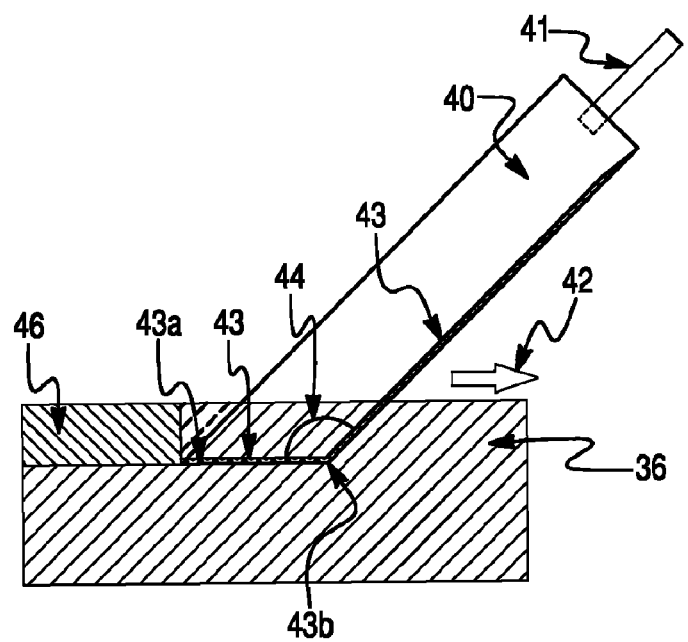
FIG. 22 portrays a side view of blade with two exposed edges at an obtuse angle in relation to making a tissue incision.
Figure 24:
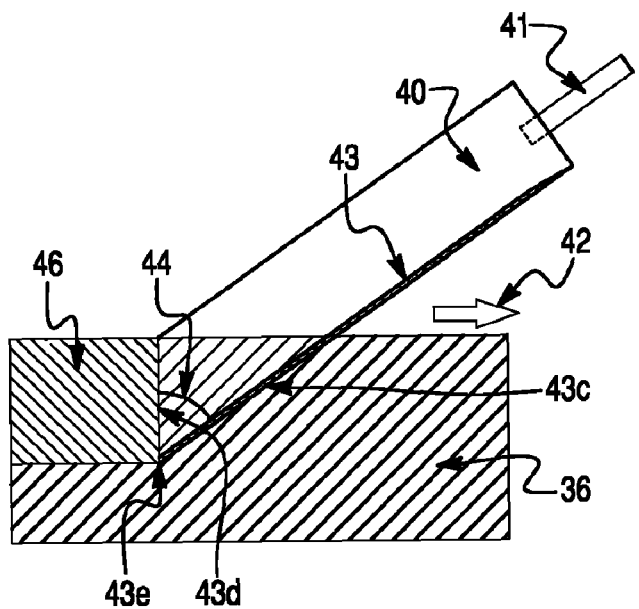
FIG. 24 portrays a side view of blade with one exposed edge in relation to making a tissue incision.

In other embodiments, the shape of the blade is configured such that when it contacts tissue and is moved through tissue, the amount of time that a tissue surface is adjacent to the functional surface is reduced or minimized. In some embodiments, the shape of the blade is configured such that it substantially has only a single line or point of contact of the functional surface with tissue. Such embodiments differ from conventional electrosurgical blades which typically allow electrosurgical energy to flow into tissue from both the edge and the sides of the blade. Some embodiments, an example of which is illustrated in FIG. 24, also differ from conventional blades that have two edges that are substantially not collinear, such as come to a form a 120 degree angle as illustrated in FIG. 21, such that one of the edges could be held approximately parallel to the tissue during use. Conventional blades of this configuration allow the same section of tissue to be exposed to electrosurgical energy over the entire time that the parallel section contacts the section of tissue, as illustrated in FIG. 22.

In various embodiments, the electrodes have functional surfaces in which the conductive elements are strictly convex in shape and thus do not contain recesses. Strictly convex surfaces do not have recesses in which tissue or electrosurgical decomposition products may become trapped. If tissue or electrosurgical decomposition products becomes momentarily trapped in a recess, such materials are exposed to electrosurgical energy and high temperature for a longer time, leading to generation of smoke and eschar. Such embodiments differ from conventional blades which have a nonconvex surface of the outer insulating surface where it extends to the edge of a metal electrode leaving the electrode slightly recessed into the insulation.

In various embodiments, one or more of the electrodes are metal with the electrodes having a thermal conductivity of at least about 0.35 W/cm ° K. Such electrode metals may comprise a metal selected from the group: gold, silver, aluminum, copper, tantalum, tungsten, columbium, and molybdenum, and alloys thereof. In various embodiments, one or more of the electrodes may be coated or plated with a substance or element that imparts resistance to oxidation, such as a plating of gold or silver.

In various embodiments, the insulation is selected and fabricated so it has a surface free energy that reduces the propensity for electrosurgical decomposition products to stick to the surface. In some embodiments, at least the edge of the conductive elements is composed of a material that reduces the propensity for electrosurgical decomposition products to stick to the surface and that is configured with a geometry that promotes the flow of thermal energy away from the edge when electrosurgical energy is being applied to tissue.

In the various embodiments, at least one electrically conductive elements is electrically connected to an ESU. When connected to an ESU, RF current will flow from the electrically conductive elements when contacting or in close proximity with an electrically conductive medium such as tissue or an electrically conductive liquid or vapor.

The various embodiments described generally above may be understood by reference to the example embodiments illustrated in the figures, which will now be described in more detail.

Referring to FIG. 12, an electrically conductive element 31, which is typically metallic, can be surrounded by insulation 32. The conductive element 31 may be of any number of shapes, such as, but not limited to: substantially flat; having one or more curves; shaped as closed curves, such as rings or hoops; shaped as nonclosed curves, such as semicircles or crescents; planar; nonplanar, such as curved spatulas; having bends or curves, such as hooks; encompassing volumes, such as cups or cylindrical volumes; substantially blunt; having one or more regions that taper from one thickness to a lesser thickness; having opposing faces, such as forceps or scissors; and having one or more openings, such as holes, meshes, pores, or coils.

Figure 25A:
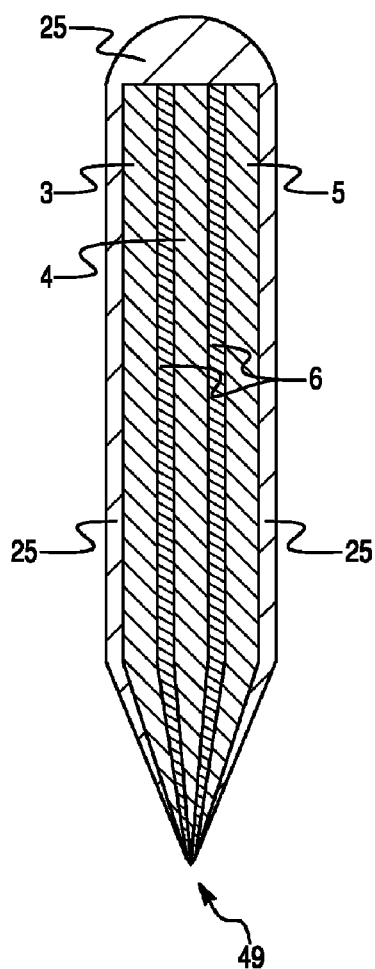
FIG. 25A-C illustrates a multielectrode electrosurgical blade according to an embodiment.
Figure 25C:
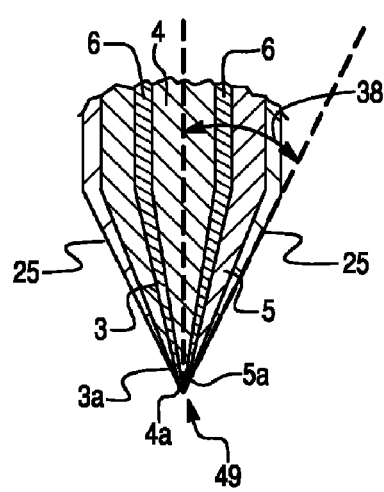
Figure 25B:
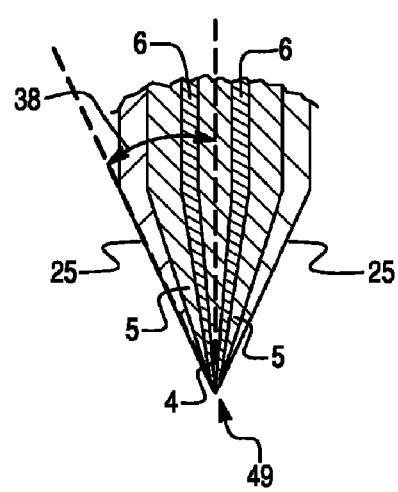

The conductive element or electrode 31 can have a tapered section 33. Additionally, the insulation 32 can have a tapered section 34. The combination of tapers on the conductive element 31 and the insulation 32 can produce bevels that transition down to the conductor edge 35 of each electrode in the blade or at least the active and return electrodes. This leaves the conductor edge 35 exposed (i.e., not covered by insulation) so that electrical energy can transfer to tissue from the edge via conduction or capacitive electrical coupling, or both conduction and capacitive coupling, including with or without other energy transfer mechanisms that may be facilitated by an exposed edge including energy conveyed by conduction or radiation or a combination of conduction and radiation. The conductive element tapered section 33 provides a cross sectional profile that reduces the width of the conductive element 31 to form the conductor edge 35 for that electrode. The tapered section 33 may be reduced on one side of the profile or both, and may take on a variety of shapes as the width is reduced. For example, the cross sectional profile of the conductive element may include a radius of curvature that produces a concave profile, as illustrated in FIG. 12. As another example, the cross sectional profile of the conductive element may have a predominately flat profile, as illustrated in FIG. 16. In a further example embodiment, the cross sectional profile may have multiple radii of curvatures producing a cross sectional profile which combines concave and convex sections. In a further example embodiment, the cross sectional profile of the outer two electrodes (i.e., the active and return electrodes) in a three electrode blade embodiment may include a radius of curvature that produces a concave profile on the exterior sides. Alternatively, the exterior surface may simply have a linear profile, as illustrated in FIGS. 25A-C. In a further example embodiment, the center passive electrode in a three electrode blade embodiment may include a linear or concave taper shape on both sides allowing the two exterior electrodes (i.e., the active and return electrodes) to be angled inward toward the blade centerline to provide a narrow tip section as illustrated in FIG. 25C.

Referring to FIG. 12, the conductor edge 35 is the portion of the conductive element 31 exposed from the insulation 32. In some embodiments, the conductor edge 5 is positioned at the edge of the blade. The conductor edge 35 is intended to be used in close proximity or touching tissue 36, as illustrated in FIG. 12. A narrow gap region 37 between the conductor edge 35 and tissue 36 is where electrosurgical energy interacts with tissue 36 via the transmission of electrosurgical energy.

In the blade configuration shown in FIG. 12, the outer profile of the tip end of the blade is approximately parabolic. As a result, in the vicinity of the conductor edge 35, the outer profile defined by the insulation 32 is relatively wide compared to the thickness of the conductor edge 35. This aspect of the blade is shown in more detail in FIG. 13.

FIG. 13 is a magnified view of the area around the narrow gap region 37 illustrated in FIG. 12. Shown are electrical conductive element 31, outer insulation 32, conductor edge 35, and tissue 36. Sparks and other means of electrosurgical energy transfer occur mostly in the primary reaction region 48, producing electrosurgical decomposition products which are depicted by the dashed arrows 39. The electrosurgical decomposition products 39 include gases, such as steam, entrained particles, and liquids that have been heated. The volume of electrosurgical decomposition products 39, particularly the gases, will increase local gas pressure in the region 48 that force the electrosurgical products out through the gap 37 formed between the tissue 36 and the combination of the blade insulation 32 and conductor edge 35. For clarity, only one conductor is shown in FIGS. 12 and 13, whereas in various embodiments multiple electrodes may be present.

The flow of the electrosurgical decomposition products 39 away from the functional area may be inhibited by the viscous drag that results from the narrowness and length of the gap 37 as well as the tortuousity of the path due to the roughness of the tissue, roughness of the blade, and contact between the tissue 36 and the insulation 32 or conductor edge 35. The more the flow of electrosurgical decomposition products 39 is inhibited, the greater the local pressure rise and the longer the reaction products remain exposed to high temperatures in the region 48. In use, tissue 36 which contacts the insulation 32 in the primary reaction region 48 may form temporary sealed pockets of gas, further inhibiting flow of reaction products. The inhibited flow from either viscous drag or temporarily sealed pockets is exacerbated when the blade is pressed into the tissue 36 by the user as a natural part of the surgical incision process. The result of these overall interactions is that the electrosurgical decomposition products in the gap region 48 between the tissue 36 and the insulation 32 and conductor edge 35 becomes pressurized to sufficient pressure to expel reaction products to achieve an approximate and temporary equilibrium between the rate of material forming and the rate of material leaving the region 48.

Even when the local pressure is high enough to force electrosurgical products from the primary reaction region 48, the resulting local temperature can be high enough to promote rapid pyrolysis and cause electropyrolysis to occur. A major constituent of many tissues is water. The conversion of water to steam is a significant absorber of energy when electrosurgical energy interacts with tissue. As a first approximation, the equilibrium temperature of saturated water and steam at the local pressure within the reactive region 48 can be used to estimate the minimum temperature that tissue in this region is exposed to during electrosurgery. For example, the estimated range of forces applied to blades by a user during an incision of tissue is about 0.15 N/mm to about 0.625 N/mm, where N/mm is Newtons per millimeter of blade movement through the tissue. If a blade has a blunt (approximately flat) profile facing the tissue (as is the case with the broad parabolic profile illustrated in FIG. 13) with a width of about 0.0508 mm (0.002 inches), then the pressure applied to the tissue when the applied force is 0.2 N/mm will be approximately 3.94 N/mm (3.94 MPA). At this pressure water boils to steam at about 250° C. (482° F.), a temperature that is high enough for tissue to pyrolyze and leave carbon-rich residues. Carbon-rich residues are those in which at least some of the electrosurgical decomposition products have a ratio of hydrogen atoms to carbon atoms less than about 1. Such carbon-rich residues are believed to be a major constituent of eschar.

The wider the contact surface in the primary reaction region 48, the greater the likelihood that tissue 36 will contact and momentarily stick to insulation 32 and the conductor edge 35, and thus, the greater the likelihood that materials will be sealed briefly in fixed volumes (e.g., pockets). As electrosurgical energy flows into a sealed volume within the reaction region 48, the equilibrium temperature will increase as pressure increases until the pressure reaches a point sufficiently high to burst through the seal of tissue stuck to the blade. Therefore, wide contact surfaces tend to lead to localized high pressure and high temperature regions as well as increase the time that electrosurgical decomposition products reside within the vicinity of the primary reaction region 48. Various embodiments use blade geometries that prevent local temperatures proximate to the conductor edge 35 from exceeding about 190° C. based upon saturated steam conditions and assuming an applied usage pressure of 0.2 N/mm. Some embodiments use blade geometries that limit the pressure on the edge of the blade to less than about 1.2 MPa.

Figure 14:
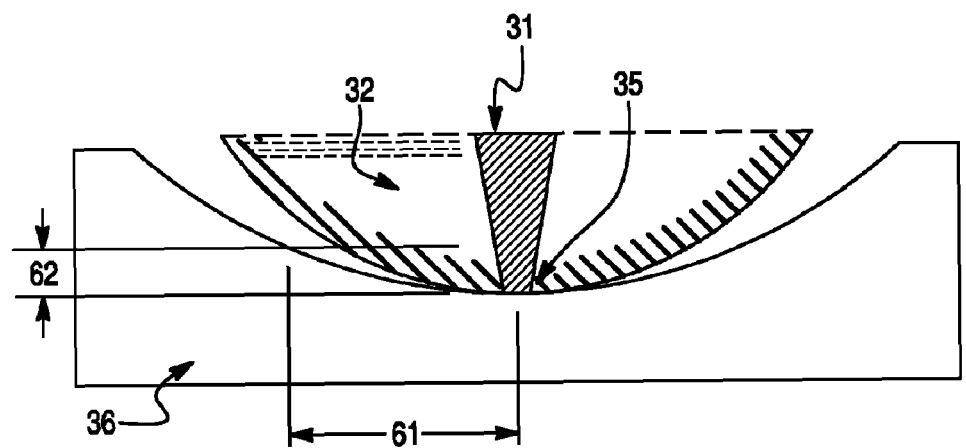
FIG. 14 portrays a magnified section of the region where electrosurgical energy interacts with tissue for the blade illustrated in FIG. 2 and shows the blade depth and half-width.

Referring to FIG. 14, some embodiments use blade geometries which include an edge depth 62 of about 0.254 mm (0.010 inches) with a blade edge half width 61 of less than about 0.5 mm (0.02 inches). In a further embodiment, the blade edge half width 61 is less than about 0.25 mm (~0.01 inches), and in yet another embodiment the blade edge half width 61 is less than about 0.12 mm (~0.005 inches).

Figure 17:
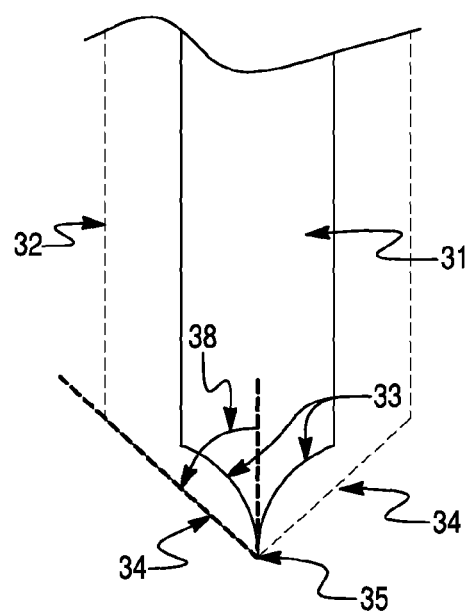
FIG. 17 portrays a cross-section of a blade with a conductive element that has a concave taper that has been insulated whereby the outer taper to the edge is not defined by a single smooth curve at the conductor edge and that shows the insulation angle.
Figure 19:
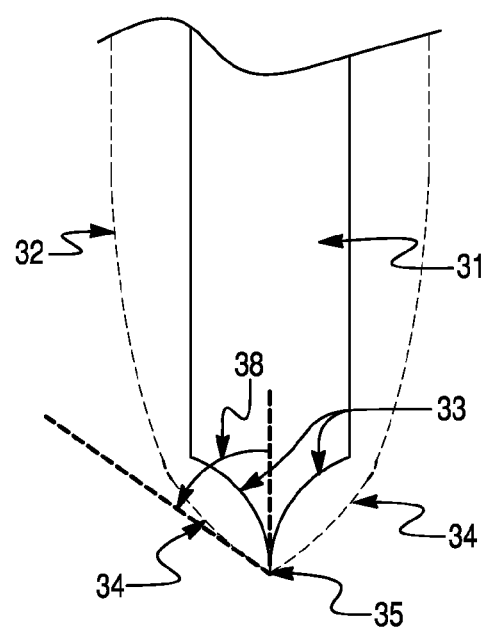
FIG. 19 portrays a cross-section of a blade with a conductive element that has a concave taper that has an overall profile that has a taper that transitions from curved to approximately flat at the edge of the blade.

To achieve reaction conditions that lead to reduced smoke and eschar, blade profiles can be used that are generally tapered in the vicinity of the edge conductor such that a tangent to the insulation at the conductor edge forms an acute angle 38 (i.e., less than 90 degrees) with the centerline of the blade as shown in FIGS. 17 and 19. Blade profiles with an acute insulation angle 38 are preferred over profiles that are of an approximately parabolic form as shown in FIG. 12. FIG. 15 and FIG. 16 illustrate geometries where the outer blade profile defined by insulation 32 is shaped with more than a single smooth curve and that join at the conductor edge 35.

FIG. 15 illustrates an embodiment where the conductive element 31 is surrounded by insulation 32 and the conductive element 31 has a concave taper 33 that results in a narrow conductor edge 35. In the embodiment illustrated in FIG. 15, the insulation 32 covering the conductive element 31 reduces in thickness toward the narrow edge until the conductive element metal is exposed forming the conductor edge 35. In this embodiment, the insulation 32 has an insulation taper 4 that also has a generally concave shape defined by the curves that smoothly terminate at the conductor edge 35. This geometry presents few opportunities for tissue to press against the edge of the blade to form seals or tortuous paths compared with the blade profile shown in FIG. 12.

FIG. 16 illustrates an embodiment similar to that shown in FIG. 15 except that the conductive element taper 33 and insulation taper 34 are approximately linear (i.e., flat) instead of being concave. As with the embodiment shown in FIG. 15, the geometry of the embodiment shown in FIG. 16 provides little opportunity for tissue to press against the edge of the blade and form seals or tortuous paths compared to the blade geometry shown in FIG. 12. Other embodiments include an insulation taper formed such that the surface of the insulation follows more than one curve defining the insulation taper in the vicinity of the conductor edge 35.

Figure 18:
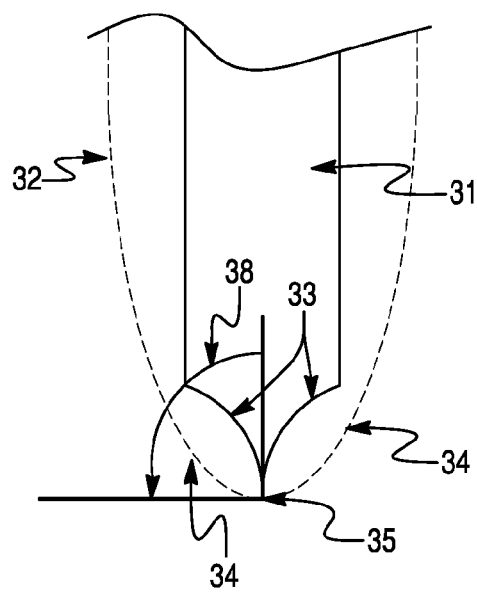
FIG. 18 portrays a cross-section of a blade with a conductive element where the outer taper to the edge is defined by a single smooth curve at the conductor edge showing the insulation angle.

FIG. 17 illustrates a blade embodiment that includes an acute insulation angle 38. The insulation angle is the angle formed between a line tangent to the insulation bevel 34 at or near the conductor edge 35 and a line parallel to the centerline of the blade. FIG. 18 illustrates the insulation angle 8 that occurs when the insulation taper 34 is be characterized by a single continuous smooth curve (a broad parabola in this case) compared to FIG. 17 where the insulation angle 38 that occurs is characterized by two curves (flat lines in this case) that essentially intersect at the conductor edge 35. FIG. 19 illustrates the case where the insulation 32 transitions from one curve to another before two separate curves intersect near the conductor tip 35 forming an acute insulation angle 38.

In the various embodiments, the insulation angle 38 should be less than 90 degrees, and preferably should be less than about 60 degrees, more preferably less than about 50 degrees, and still more preferably less than about 45 degrees.

Figure 20:
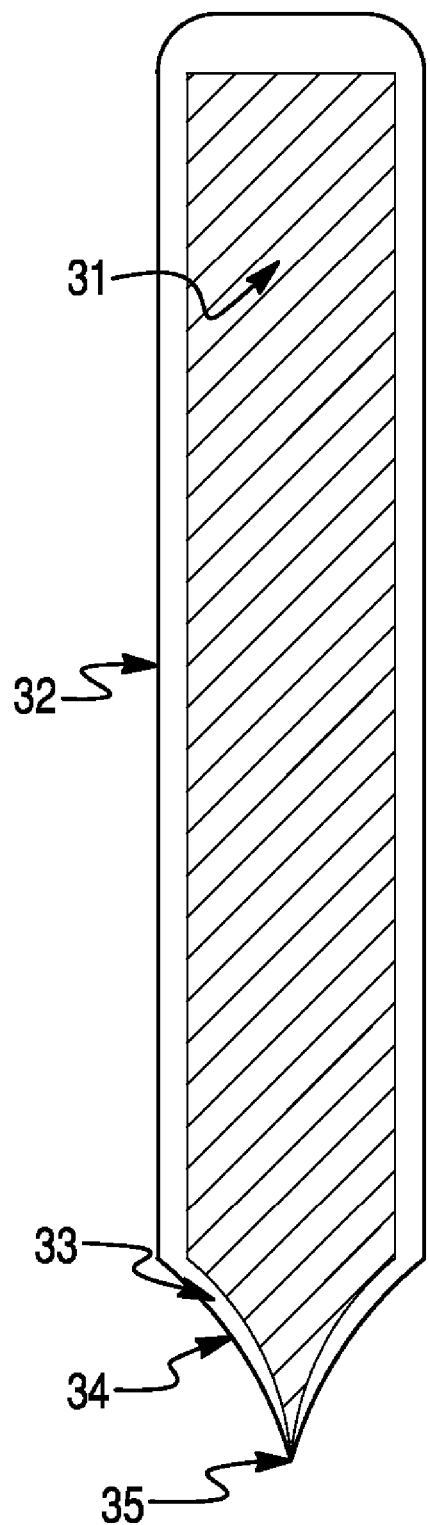
FIG. 20 portrays a cross section of a blade having a conductive element that has a concave taper and a concave overall taper to an edge.

A number of geometries for the taper portion can be employed to achieve an insulation angle of less than 90 degrees. FIG. 14 illustrates a narrow parabola geometry with an acute insulation angle. FIG. 15 illustrates a concave geometry which results in an acute insulation angle. FIGS. 16 and 17 illustrate a flat (i.e., linear) taper with an acute insulation angle. FIG. 19 illustrates a two-curve geometry resulting in an acute insulation angle. FIG. 20 illustrates a blade cross-section that has an insulation taper 34 that is concave. FIG. 20 also illustrates a conductive element 31 with a concave tapered region 33 that reduces down to form the conductor edge 35. Embodiments with conductive elements that have substantially concave tapers down to the edge facilitate the production of an outer insulation profile that is also concave as FIG. 20 illustrates.

The blade thickness profile embodiments illustrated in FIGS. 12-20 can be used for a cutting blade with a planar shape similar to a scalpel, in which case the width of the blade would extend out of the page.

Restricting the amount of time that tissue and electrosurgical decomposition products are exposed to electrosurgical energy reduces the amount of eschar and smoke produced and reduces the amount of tissue damage. When the edge of blade contacts tissue for a period of time longer than is necessary to achieve the predetermined surgical effect, such as cutting, then more smoke and eschar are produced and more tissue damage occurs. The various embodiments include insulation 32 over the conductive element 31 which insulates the outside of the blade except for the exposed conductor edge 35, as has been illustrated in FIGS. 12-20. The insulation 32 restricts the flow of electrosurgical energy from the conductive element 31 to the tissue 36 except at the conductor edge 35. To serve this function, the insulation 32 needs to be of an adequate dimension so as to restrict or prevent the flow electrosurgical energy. However, too much insulation may make the blade width excessive.

The conductive element 31 both conveys electrical energy to the conductor edge 35 and conducts thermal energy away from the conductor edge 35 to help keep the blade relatively cool. Making the conductor edge 35 thick would facilitate conducting heat away from the edge, but if the edge is too thick then more sealing of tissue against the edge can occur with the coincident increase in smoke and eschar production and tissue damage. The ability of the conductive element 31 to remove thermal energy from the conductor edge 35 depends on the thermal conductivity of the material from which it is made. This relationship between thermal conductivity and the width of the edge can be expressed as the product of thermal conductivity and the width of the conductor edge 35, such that a poorer thermal conductor needs a wider path than a better thermal conductor. As used herein, the term "thermal path conductance" refers to the product of the conductive element material's thermal conductivity and the width of the thermal flow path, where the thermal conductivity is measured in W/m/° K at about 300° K and the width is measured in meters, leading to the units of thermal path conductance being W/° K. Tthe various embodiments can have a thermal path conductance at the conductor edge of at least 0.0002 W/° K, preferably of at least 0.0003 W/° K, more preferably of at least 0.0006 W/° K, and still more preferably of at least 0.001 W/° K. For example, if the thermal path width is 0.0005 inches (1.27E-5 m) and the material used is molybdenum having a thermal conductivity of about 138 W/m/° K, then the thermal path conductance is about 0.00175 W/° K. In a blade having a planar configuration like a scalpel, the width of the thermal path will be the thickness of the blade at the edge.

To reduce the amount of tissue heated, the electrosurgical energy is focused in the various embodiments. One method of focusing the energy is to insulate the blade except for an exposed edge. Preferably, the exposed conductor edge 35 of the conductive element 31 is flush with the insulation layer 32 so as to avoid any recessed pockets and an unnecessarily broad reaction area such as formed if the electrode is recessed into a pocket in the insulation, the edge is coated with an insulator, or the edge is rounded. In some embodiments, the conductor edge 35 adjoins the insulating layer 32 to form a singular tapered exterior surface. Focusing electrosurgical energy is further facilitated by having a narrow conductor edge 35.

A flush, non-recessed conductor edge 35 further facilitates the electrosurgical process beyond the focus of electrosurgical energy. If the conductor edge is recessed within the insulation, then a pocket exists where tissue or electrosurgical decomposition products can accumulate and remain exposed for long durations to electrosurgical energy, thus promoting continued pyrolysis and electropyrolysis. In an embodiment, no pockets or recesses exist where tissue or electrosurgical decomposition products can accumulate. Therefore, gaps or recesses between the conductor edge and the insulation are avoided in various embodiments. By adjoining the conductor edge with the insulating layer to form a flush exterior tapered surface with no gaps or recesses, the singular exterior tapered surface can take on a strictly convex shape immediately adjacent to the conductor edge. This embodiment reduces or eliminates opportunities for trapping tissue during use. Away from the conductor edge the profile of the insulation taper can be concave. This embodiment reduces residency time at high temperatures and reduces pressure which reduces the equilibrium steam temperature.

In addition to avoiding gaps or recess between the conductor edge 35 and the insulation layer 32, the conductor edge 35 itself should not have recesses in the conductive element material that might promote the trapping of tissue or electrosurgical decomposition products. Preferably the conductor edge 35 is relatively smooth and does not have recesses along its length or width, such sawtooth, gaps, pockets or holes that are larger than about 32 microinches.

Embodiments of the invention include conductor edge shapes that are pointed, terminate to an acute angle, or are flat. Preferably, the shape of the conductor edge 35 is not rounded. Preferably the conductor edge has a thickness less than about 0.005 inches, more preferably less than about 0.002 inches, more preferably less than about 0.001 inches, and even more preferably about 0.0005 inches or less.

The thickness of the insulation layer, particularly at the area proximate to the conductor edge, affects the overall thickness of the edge of the blade. Enough insulation needs to be present to restrict the rate of energy transfer out the sides of the blade into tissue or electrosurgical decomposition products to prevent or reduce continued changes in those materials. Restricting the rate of energy transfer out the sides is particularly important near the conductor edge where temperatures will be highest. If the insulation is thicker than necessary to prevent continued changes in tissue or electrosurgical decomposition products, then the blade will be wider than necessary near the conductor edge, which increases the opportunities for sealing tissue against the conductor edge or the insulation near the conductor edge.

When conductive element 31 is tapered so that it is thinnest at the conductor edge 35, as illustrated in FIGS. 12-20, the temperature of the conductive element will decrease as the distance from the conductor edge 35 increases. Therefore, the thickest insulation needs to be near the conductor edge 35, allowing the shape of the insulation 32 to have a tapered region 4 that needs to be no thicker than it is near the conductor edge 35. The thickness of the insulation at the conductor edge can be at least one half of the thickness of the conductor edge and more preferably at least equal to about the thickness of the conductor edge. For example, if the conductor edge can have a thickness of 0.001 inches then the insulation surrounding the conductor edge preferably has a thickness of about 0.0005 inches and preferably has a thickness of about 0.001 inches.

The main portion of the conductive element 31 should be thick enough to readily conduct heat away from the conductor edge 35. The width of the conductive element 31 can have a thickness before the taper portion 33 that is at least about 5 times as thick as the conductor edge 35, preferably at least about 10 times as thick as the conductor edge 35, and more preferably at least about 20 times as thick as the conductor edge 35. For example, if the conductor edge is 0.001 inches thick and the conductive element thickness before the taper begins is 0.020 inches, then the ratio of the thickness of the conductive element to the thickness of the conductor edge 35 is 20.

Figure 23:
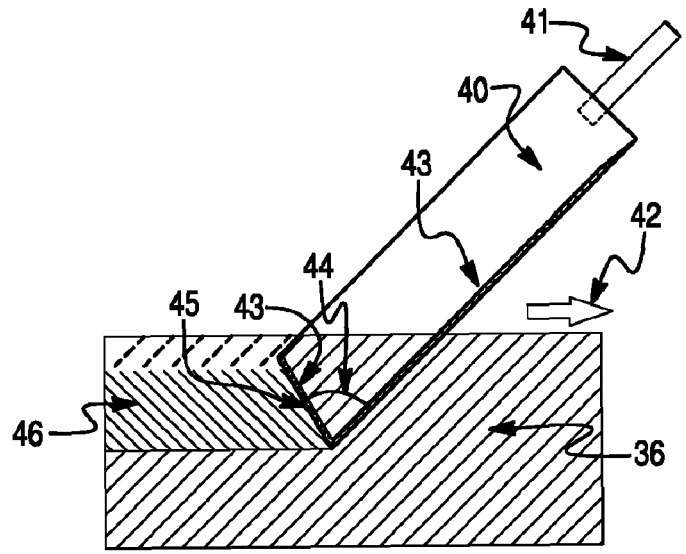
FIG. 23 portrays a side view of blade with two exposed edges at an acute angle in relation to making a tissue incision.

In addition to the edge geometry, the overall configuration of the blade contributes the generation of excessive decomposition products and increased tissue damage. For example, FIG. 21 illustrates a blade connected to shaft 41 that has blade body 40 with intersecting active edges 43 that subtend intersecting edge angle 44. As used herein, the term "active edge" refers to a blade edge having a two or more conductor edges which transmit electrosurgery energy to tissue. In use, the blade produces the predetermined surgical effect (e.g., cutting) when the blade is moved through tissue in the direction indicated by arrow 42. This blade configuration moving through tissue 36 is illustrated in FIG. 22. As the blade 40 moves through tissue, an electrosurgically affected tissue region 16 is created. As the blade 40 moves through tissue 36, the leading corner 43b initially contacts the tissue near the bottom of the blade and bottom edge 43a then continues to supply electrosurgical energy to the already affected tissue as the blade is moved. Thus, the bottom active edge 43a prolongs the residence time that the tissue along bottom active edge 43a is affected by electrosurgical energy. The prolonged residence time increases smoke and eschar production and increases tissue damage. The intersecting edge angle 44 influences whether such prolonged residence time occurs and the closer that the angle is to 180 degrees (i.e., the less there is a trailing edge) the less likely that prolonged residence time occurs. If the intersecting edge angle 44 is made more acute, the situation depicted in FIG. 23 occurs. While the residence time of tissue near the trailing edge 45 is reduced in the configuration illustrated in FIG. 23, the trailing active edge 45 following the incision does continue supplying electrosurgical energy to tissue 46 that has already been affected by electrosurgical energy delivered from the leading edge 43.

The intersecting active edges 43 in FIGS. 21-24 provide a point of concentration for electrosurgical energy when the blade first contacts tissue 6 facilitating starting an electrosurgical effect such as cutting. Thus, such a concentration is desirable because it makes starting or controlling the electrosurgical effect easier. In various embodiments, the intersecting active edges angle does not allow the blade to be oriented during use that tissue is exposed to an active edge (and thus exposed to electrosurgical energy) for a prolonged residence time. In some embodiments, the intersecting edge angle is obtuse, in some embodiments the intersecting edge angle is greater than about 160 degrees, and in an embodiment the intersecting edge angle is approximately equal to about 180 degrees. The example embodiment geometries illustrated in the figures show edges that are substantially straight. Other embodiments include edges that have one or more curves, such as edges comprised of one or more parts of ellipses, circles, parabolas, or hyperbolas, and edges composed of a multiplicity of straight sections as well as edges composed of one or more combinations of straight sections and curves.

In an embodiment, only one active edge is present as illustrated in FIG. 24. The single active edge 43 is also the leading edge 43c that first transfers electrosurgical energy to tissue 6 producing the electrosurgically affected tissue region 46. The trailing edge 43d is not a active edge, i.e., it does not transfer electrosurgical energy to tissue because it does not have an exposed surface (conductor edge) capable of transferring electrosurgical energy to tissue. The blade illustrated in FIG. 24 comes to a region 43e where electrosurgical energy is concentrated when the blade first contacts tissue 36.

In various embodiments, the blade has one or more active edges configured so that they cause electrosurgical energy to enter tissue only at the time when the blade first encounters tissue that has not yet experienced the predetermined electrosurgical effect. In some embodiments, the blade has one or more active edges configured so that they have a region that concentrates electrosurgical energy when the blade first contacts tissue, such as in a region that approximates a point, and such blade has two or more active edges configured so that they cause electrosurgical energy to enter tissue only at the time when the blade first encounters tissue that has not yet had the predetermined electrosurgical affect occur. For embodiments where the blade is to be used as a scalpel for cutting and other electrosurgical functions, the embodiments may have two active edges that comes to a point approximately.

In various embodiments, the benefits of the bipolar blade are combined with the benefits provided by the blade geometry and material to provide a bipolar blade that exhibits further reduced smoke and eschar generation. An example embodiment of such a combination is illustrated in FIGS. 25A-C. Referring to FIG. 25A, the blade includes an active electrode 3, passive electrode 4, and return electrode 5 which taper to narrow conductor edges 3a, 4a, 5a. The conductor edges 3a, 4a, 5a are formed where the electrodes emerge from the insulation 25 cover. The exposed regions of the electrodes can vary and the lengths of the blades can be stepped or otherwise made unique to facilitate producing electrical contact surfaces. Referring to FIG. 25B, the electrodes can be configured to provide an acute insulation angle 38. For example, as illustrated in FIG. 25B, electrodes 3 and 5 can be shaped with a convex shape in the taper. Additionally, the insulation 25 can be tapered with an convex shape. The combination of the tapers in the electrodes 3 and 5 and the insulation 25 provides a narrow active edge 49 with an acute insulation angle 38 to facilitate flow of decomposition products from the active region. Another example illustrated in FIG. 25C includes electrodes 3, 4 and 5 which are shaped with a linear (i.e., flat) taper to a narrow conductor edge. The insulation 25 also features a linear taper to a narrow active edge 49 that features an acute insulation angle 38. The interblade insulation 6 can be provided down to active edge 49 to prevent a short circuit among electrodes 3, 4 and 5, and can be tapered or not tapered.

By employing various embodiments, a higher crest factor electrosurgical energy can be used for the predetermined surgical effect of cutting without excessive damage to tissue or generation of smoke or eschar. Crest factor is the ratio of peak voltage to the root mean square (RMS) voltage. During cutting, crest factors of less than about 5 and typically less than about 3 are used. For a predetermined surgical effect of moderate coagulation crest factors of about 4 to 5 are typically used. To achieve the predetermined surgical effect of aggressive coagulation, crest factors greater than 8, typically of about 9, are used. If cutting tissue is attempted with crest factors that are too high, the cutting effect will be very poor and blades that do not incorporate features of the various embodiments will immediately accumulate large masses of adherent tissue that prevents further use until the blade is cleaned. Thus, the drawbacks of conventional electrosurgical blades prevent the use of high crest factors for cutting. By focusing electrosurgical energy and reducing the residence time during which tissue is exposed to electrosurgical energy the various embodiments of the present invention allow use of higher crest factors for cutting.

Using high crest factors for cutting enhances hemostasis. Enhancing hemostasis is particularly beneficial when the tissue being affected is highly vascularized, such as the liver. One embodiment provides a blade that cuts with enhanced hemostasis that comprises an insulated conductive element that tapers to one or more conductor edges that are at least partially exposed such that they can transfer electrosurgical energy to tissue and that have thermal path conductance that is at least 0.0002 W/° K, wherein the exposed edge is no thicker than about 0.005 inches and the blade is connected to an ESU configured to supply electrosurgical power with a crest factor of 5 or larger.

In various embodiments, the outer insulating layer may have a maximum thermal conductance of about 1.2 W/cm$^{2\circ}$ K when measured at about 300° K, preferably about 0.12 W/cm$^{2\circ}$ K or less when measured at about 300° K, and more preferably about 0.03 W/cm$^{2\circ}$ K when measured at about 300° K. As used herein, thermal conductance refers to a measure of the overall thermal transfer across any given cross section (e.g. of the insulation layer), taking into account both the thermal conductivity of the materials comprising such layer and the thickness of the layer (i.e. thermal conductance of layer=thermal conductivity of material comprising the layer (W/cm ° K)/thickness of the layer (cm)).

In relation to the various embodiments, the insulation layer should also exhibit a dielectric withstand voltage of at least the peak-to-peak voltages that may be experienced by the electrosurgical instrument during surgical procedures. The peak voltages will depend upon the settings of the RF source employed, as may be selected by clinicians for particular surgical procedures. In various embodiments, the insulation layer should exhibit a dielectric withstand voltage of at least about 50 volts, and more preferably, at least about 150 volts. As used herein, the term "dielectric withstand voltage" means the capability to avoid an electrical breakdown (e.g. an electrical discharge through the insulating layer) for electrical potentials up to the specified voltage.

In some embodiments, the insulating or electrode bonding layer may comprise a porous ceramic material that has had at least the pores on the surface sealed to prevent or impede the penetration of biological materials into the pores. Such ceramic may be applied to the electrodes via dipping, spraying, etc, followed by curing via drying, firing, etc. Preferably, the ceramic insulating layer should be able to withstand temperatures of at least about 2000° F.

The ceramic insulating layer may comprise various metal/non-metal combinations, including for example compositions that comprise the following: aluminum oxides (e.g. alumina and $Al_2O_3$), zirconium oxides (e.g. $Zr_2O_3$), zirconium nitrides (e.g. ZrN), zirconium carbides (e.g. ZrC), boron carbides (e.g. $B_4C$), silicon oxides (e.g. $SiO_2$), mica, magnesium-zirconium oxides (e.g. $(Mg-Zr)O_3$), zirconium-silicon oxides (e.g. $(Zr-Si)O_2$), titanium oxides (e.g., $TiO_2$) tantalum oxides (e.g. $Ta_2O_5$), tantalum nitrides (e.g. TaN), tantalum carbides (e.g., TaC), silicon nitrides (e.g. $Si_3N_4$), silicon carbides (e.g. SiC), tungsten carbides (e.g. WC) titanium nitrides (e.g. TiN), titanium carbides (e.g., TiC), nibobium nitrides (e.g. NbN), niobium carbides (e.g. NbC), vanadium nitrides (e.g. VN), vanadium carbides (e.g. VC), and hydroxyapatite (e.g. substances containing compounds such as $3Ca_3(PO_4)_2Ca(OH)_2Ca_{10}(PO_4)_6(OH)_2Ca_5(OH)(PO_4)_3$, and $Ca_{10}H_2O_{26}P_6$). One or more ceramic layers may be employed, wherein one or more layers may be porous, such as holes filled with one or more gases or vapors. Such porous compositions will usually have lower thermal conductivity than nonporous materials. An example of such materials is foam, such as an open cell silicon carbide foam. Such porous materials have the disadvantage that they allow fluids, vapors, or solids to enter the pores whereby they are exposed to prolonged contact with high temperatures which can lead to thermal decomposition or oxidation and produce smoke or other noxious or possibly dangerous materials. Sealing the surface of the ceramic prevents such incursions, while substantially preserving the beneficial reduced thermal conductivity of the pores.

Ceramic coatings or electrode bonding materials may also be formed in whole or part from preceramic polymers that when heated form materials containing Si—O bonds able to resist decomposition when exposed to temperatures in excess of 1200° F., including compositions that use one or more of the following as preceramic polymers: silazanes, polysilzanes, polyalkoxysilanes, polyureasilazane, diorganosilanes, polydiorganosilanes, silanes, polysilanes, silanols, siloxanes, polysiloxanes, silsesquioxanes, polymethylsilsesquioxane, polyphenyl-propylsilsesquioxane, polyphenylsilsesquioxane, polyphenyl-vinylsilsesquioxane. Preceramic polymers may be used to form the ceramic coating by themselves or with the addition of inorganic fillers such as clays or fibers, including those that contain silicon oxide, aluminum oxides, magnesium oxides, titanium oxides, chrome oxides, calcium oxides, or zirconium oxides.

Ceramic coatings may also be formed by mixing one or more colloidal silicate solutions with one or more filler materials such as one or more fibers or clays. The filler materials can contain one or more materials that have at least 30 percent by weight $Al_2O_3$ or $SiO_2$ either alone or combined with other elements, such occurs in kaolin or talc. The colloidal silicate and filler mixture may optionally contain other substances to improve adhesion to electrode surfaces or promote producing a sealed or hydrophobic surface. Representative examples of colloidal silicate solutions are alkali metal silicates, including those of lithium polysilicate, sodium silicate, and potassium silicate, and colloidal silica. Fibers may include those that contain in part or wholly alumina or silica or calcium silicate, and Wollastonite. Clays may include those substances that are members of the smectite group of phyllosilicate minerals. Representative examples of clay minerals include bentonite, talc, kaolin (kaolinite), mica, clay, sericite, hectorite, montmorillonite and smectite. Various embodiments use at least one of kaolin, talc, and montmorillonite. These clay minerals can be used singly or in combination. In various embodiments, at least one dimension, such as diameter or particle size, of at least one of the filler materials has a mean value of less than 200 micrometers and more preferably has a mean value of less than 50 micrometers and even more preferably has a mean value of less than 10 microns and still more preferably has a mean value less than 5 microns Substances that may be added to promote adhesion or production of a sealed or hydrophobic surface include those that increase the pH of the mixture, including sodium hydroxide or potassium hydroxide, and hydrolysable silanes that condense to form one or more cross-linked silicone-oxygen-silicon structures.

Sealing a porous insulator is accomplished not by coating the ceramic in the sense that electrosurgical accessories have been coated with PTFE, silicone polymers and other such materials. Best surgical performance occurs when accessories are thin, therefore pores are best filled by a material that penetrates the surface of the porous material and seals the pores. Some residual material may remain on the surface, but such material is incidental to the sealing process.

Sealing materials need to withstand temperatures exceeding 400° F. and more preferably withstand temperatures exceeding 600° F. Silicates and solutions containing or forming silicates upon curing can be used. Other materials may be used, including silicone and fluorosilicones. For sealing, the materials need to have low viscosity and other properties that enable penetration into the surface of the porous insulator. Traditional silicone and fluorosilicone polymer-forming compounds do not have these properties unless they are extensively diluted with a thinning agent, such as xylene or acetone.

A sealed porous insulation may be employed to yield an average maximum thermal conductivity of about 0.006 W/cm-° K or less where measured at 300° K. The insulating layer outside of the blade may have a thickness of between about 0.001 and 0.2 inches, and preferably between about 0.005 and 0.100 inches and more preferably between about 0.005 and 0.050 inches.

A coating that is applied as a single substance that upon curing does not require sealing may also be used for the outer insulation or as the bonding material between electrodes. Examples of such coatings include those formed from mixtures that use one or more of the aforementioned colloidal silicates and clays and also use one or more substances that reduce the surface free energy of the surface. Substances that reduce the surface free energy include: halogenated compounds, fluoropolymer compounds, such as PTFE and PFA, including aqueous dispersions of such compounds; and organofunctional hydrolysable silanes, including those containing one or more fluorine atoms on one or more pendant carbon chains.

In some embodiments, a hydrolysable silane is a component in the coating or in the insulating material between electrodes, with the hydrolysable silane having one or more halogen atoms and having a general formula of $CF_3(CF_2)_m(CH_2)_n Si(OCH_2CH_3)_3$ where m is preferably less about 20 and more preferably about 5 or less and where n is preferably about 2. Other groups besides $(OCH_2CH_3)_3$, such as those based on ethyl groups, may be used and fall within the scope of the various embodiments when they also are hydrolysable. Other halogens, such as chlorine, may be substituted for the fluorine, although these will typically produce inferior results.

Preferably, the surface energy (also referred to as the surface tension or the surface free energy) of the coating is less than about 32 millinewtons/meter and more preferably less than about 25 millinewtons/meter and even more preferably less than about 15 millinewtons/meter and yet more preferably less than about 10 millinewtons/meter.

In an embodiment, the conductive elements or conductor edges or both of the electrosurgical instrument may be configured to have a thermal conductivity of at least about 0.35 W/cm ° K when measured at about 300° K. By way of example, the conductive elements or conductor edges or both may comprise at least one metal selected from the group including: silver, copper, aluminum, gold, tungsten, tantalum, columbium (i.e., niobium), and molybdenum. Alloys comprising at least about 50% (by weight) of such metals may be employed, and even more preferably at least about 90% (by weight). Additional metals that may be employed in such alloys include zinc.

In various embodiments, at least a portion of the conductor edge is not insulated (i.e. not covered by the outer insulating layer). In connection therewith, when the conductor edge comprises copper, the exposed portion may be coated or plated (e.g. about 10 microns or less) with a biocompatible metal. By way of example, such biocompatible metal may be selected from the group including: nickel, silver, gold, chrome, titanium tungsten, tantalum, columbium (i.e., niobium), and molybdenum.

In some embodiments, the conductive element, conductor edge, or both may comprise two or more layers of different materials. More particularly, at least a first metal layer may be provided to define at least part of the conductor edge that is functional to convey electrosurgical energy to tissue as described above. Such first metal layer may comprise a metal having a melting temperature greater than about 2600° F., preferably greater than about 3000° F., and more preferably greater than about 4000° F., thereby enhancing the maintenance of a desired peripheral edge thickness during use (e.g. the outer extreme edge noted above). Further, the first metal layer may have a thermal conductivity of at least about 0.35 W/cm ° K when measured at 300° K.

For living human/animal applications, the first metal layer may comprise a first material selected from a group including: tungsten, tantalum, columbium (i.e., niobium), and molybdenum. All of these metals have thermal conductivities within the range of about 0.5 to 1.65 W/cm ° K when measured at 300° K. Alloys comprising at least about 50% by weight of at least one of the group of materials may be employed, and more preferably at least about 90% by weight.

In addition to the first metal layer, the conductive element may further comprise at least one second metal layer on the top and/or bottom of the first metal layer. A first metal layer as noted above can be provided in a laminate arrangement between top and bottom second metal layers. To provide for rapid heat removal, the second metal layer(s) preferably has a thermal conductivity of at least about 2 W/cm ° K. By way of example, the second layer(s) may advantageously comprise a second material selected from the group including: copper, gold, silver and aluminum. Alloys comprising at least about 50% of such materials may be employed, and more preferably at least about 90% by weight. It is also preferable that the thickness of the first metal layer and of each second metal layer (e.g. for each of a top and bottom layer) be between about 0.001 and 0.25 inches, and even more preferably between about 0.005 and 0.1 inches.

One or more of the conductor edges may be plated with gold or silver or alloys thereof to confer added oxidation resistance to the portions of the electrodes exposed to tissue or current flow or both. Such plating may be applied using electroplating, roll-bonding or other means either after assembly or prior to assembly of the electrodes to form blades. The plating thickness can be at least about 0.5 micrometers and preferably at least about 1 micrometer.

As may be appreciated, multi-layered metal bodies of the type described above may be formed using a variety of methods. By way of example, sheets of the first and second materials may be roll-bonded together then cut to size. Further, processes that employ heat or combinations of heat and pressure may also be utilized to yield a laminated electrode.

In some embodiments, the electrosurgical instrument may further comprise a heat sink for removing thermal energy from the conductor edge, conductive element, or both. In this regard, the provision of a heat sink helps establishes a thermal gradient for conducting heat away from the conductor edge, thereby reducing undesired thermal transfer to a tissue site. More particularly, it is preferable for the heat sink to operate so as to maintain the maximum temperature on the outside surface of the insulating layer at about 160° C. or less, more preferably at about 80° C. or less, and most preferably at 60° C. or less. Relatedly, it is preferable for the heat sink to operate to maintain an average conductive element temperature of about 500° C. or less, more preferably of about 200° C. or less, and most preferable of about 100° C. or less.

In an embodiment, the heat sink may comprise a vessel including a phase change material that either directly contacts a portion of the electrodes (e.g. a support shaft portion) or that contacts a metal interface provided on the vessel which is in turn in direct contact with a portion of the electrodes (e.g. a support shaft portion). Such phase change material changes from a first phase to a second phase upon absorption of thermal energy from the electrodes. In this regard, the phase change temperature for the material selected should preferably be greater than the room temperature at the operating environment and sufficiently great as to not change other than as a consequence of thermal heating of the electrosurgical instrument during use. Such phase change temperature should preferably be greater than about 30° C. and most preferably at least about 40° C. Further, the phase change temperature should be less than about 225° C. Most preferably, the phase change temperature should be less than about 85° C.

The phase change may be either from solid to liquid (i.e., the phase change is melting) or from liquid to vapor (i.e., the phase change is vaporization) or from solid to vapor (i.e., the phase change is sublimation). More practical phase changes to employ are melting and vaporization. By way of example, such a phase change material may comprise a material that is an organic substance (e.g., fatty acids, such as stearic acid, hydrocarbons such as paraffins) or an inorganic substance (e.g., water and water compounds containing sodium, such as, sodium silicate (2-)-5-water, sodium sulfate-10-water).

In an embodiment, the heat sink may comprise a gas flow stream that passes in direct contact with at least a portion of the electrodes. Such portion may be a peripheral edge portion and/or a shaft portion of the electrodes that is designed for supportive interface with a holder for hand-held use. Alternatively, such portion may be interior to at least a portion of the electrodes, such as interior to the exposed peripheral edge portion and/or the shaft portion of the electrodes that is designed for supportive interface with a holder for hand-held use. In yet other embodiments, the heat sink may simply comprise a thermal mass (e.g. disposed in a holder).

In an embodiment, an electrosurgical instrument comprises a main body portion having a blade-like configuration at a first end and an integral, approximately cylindrical shaft at a second end. The main body may comprise a highly-conductive metal and/or multiple metal layers as noted. At least a portion of the flattened blade end of the main body can be coated with a ceramic-based and/or silicon-based, polymer insulating layer, except for the peripheral edge portion thereof. The cylindrical shaft of the main body can be designed to fit within an outer holder that can be adapted for hand-held use by medical personnel. Such holder may also include a chamber comprising a phase-change material or other heat sink as noted hereinabove. Additionally, electrical, push-button controls may be incorporated into the holder for selectively controlling the application of one or more, predetermined, electrosurgical signal(s) from an RF energy source to the blade via the shaft of the main body portion.

Figure 26:
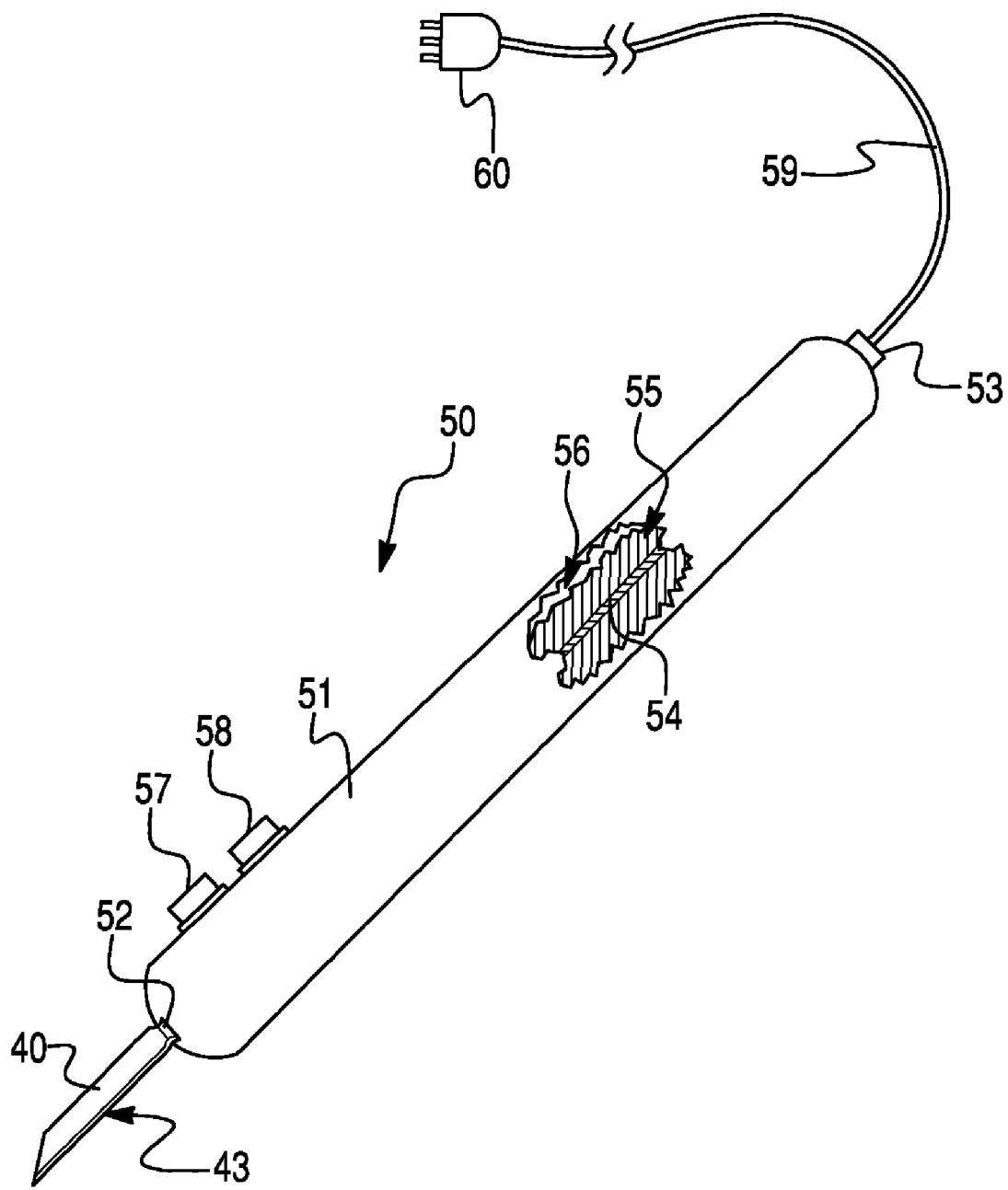
FIG. 26 illustrates an electrosurgical instrument including a holder and blade according to an embodiment.

In the various embodiments, the active, return and passive electrodes with their surrounding insulation are provided as a single use (e.g., intended to be discarded after a single use) or disposable blade 40 that is configured to be coupled to a reusable or single use holder or handle 51 to form an electrosurgical instrument assembly 50 as illustrated in FIG. 26. The blade 40 includes electrical connector surfaces on the proximal end (i.e., the end of the electrodes closest to the handle in use) configured to electrically connect each of the active, return and passive electrodes to compatible electrical connector surfaces 52 in the handle 51, such as sleeve contactors within the holder or handle 51. The connector 52 surfaces may also serve as a mechanical coupling so that by inserting the blade 40 into the blade-to-holder connector 52, the blade 40 is rigidly held by the holder 51. Similarly, the connector 52 or handle 51 may include a disconnection mechanism to allow the blade 40 to be readily disconnected from the holder 51. An electrical connector 53 on the handle 51 can be provided to connect, such as by means of a cable 59, to an ESU or similar source of radio frequency (RF) AC power. An internal set of conductors 54 conduct RF power from the connector 53 at one end of the handle 51 to the blade-to-holder connector 52 at the other end of the handle 51. The internal conductors 54 and the blade-to-handle connector 52 include separate electrical paths and are configured to connect the RF power and connect a negative voltage source to each of the active and return electrodes and connect a positive voltage source to the passive electrode. In an embodiment, the electrical connector 53 and cable 59 may also connect the handle 51 to a DC power source for providing a negative voltage for connection to the active and return electrodes and a positive voltage for connection to the passive electrode by way of the internal conductors 54 and the blade-to-handle connector 52. In an embodiment, the handle 51 includes a rectifier circuit, such as described herein, connected to the internal conductors 54 or electrical connector 53 to receive RF power and output DC current with the negative voltage provided to the active and return electrodes and the positive voltage provided to the passive electrode by way of the blade-to-handle connector 52. Electrical and thermal insulation 55 can be provided to isolate power being conducted in the internal conductors 54 from the handle exterior 56, thereby protecting the clinician using the assembly. The blade connectors 52 may also include electrical insulation to electrically isolate the blade 40 from the handle exterior 56. One or more control components, such as buttons or switches 57, 58, for controlling power or other aspects of the device's operation may be provided on the handle 51 to enable a user to activate, deactivate and otherwise control power provided by the ESU or RF power source. The handle 51 may be shaped to enable a user to comfortably hold or otherwise manipulate the assembly 50, provided with a surface material or surface texture, such as roughening, to enhance a user's grip and other ergonomic features to aid a clinician in manipulating the disposable electrosurgical assembly 50. The handle 51 may be reusable or a single use disposable device. A cable 59 connectable to the connector 53 and fitted with a suitable electrical plug 60 can be used to electrically couple the assembly 50 to an ESU. The cable 59 may be reusable or disposable. In an embodiment, the cable 59 and plug 60 are included as part of a single use electrosurgical assembly 50. In an embodiment including one or more control elements 57, 58 on the handle 51, electronic connectors may be provided within cable 59 for relaying control signals to the ESU.

In some embodiments, a single use sterile disposable 40 blade can be sealed in a sterile package, which may include a cable 59 and/or instructions for assembly and use, to provide an electrosurgical kit to be opened at the time surgery is to be performed. In an embodiment, a handle 51 is also included in the sterile package.

Conventional electrosurgical signals may be advantageously employed in combination with one or more of the above-noted electrosurgical instrument embodiments. In particular, the inventive electrosurgical instrument yields benefits when employed with electrosurgical signals and associated apparatus of the type described in U.S. Pat. No. 6,074,387, hereby incorporated by reference in its entirety.

The apparatus and methods for reducing smoke, eschar, and tissue damage according to various embodiments may be applied in conjunction with other methods for reducing the local heating that promotes the excessive electrosurgical tissue decomposition which leads to smoke, eschar, and tissue damage. Such additional methods for reducing local heating include providing for an effective level of heat removal away from functional portions of an electrosurgical instrument and/or by otherwise enhancing the localized delivery of an electrosurgical signal to a tissue site, such as by reducing the exposed areas of either or both functional and nonfunctional areas by using thermal insulation.

While the present invention has been disclosed with reference to certain preferred embodiments, numerous modifications, alterations, and changes to the described embodiments are possible without departing from the sphere and scope of the present invention, as defined in the appended claims. Accordingly, it is intended that the present invention not be limited to the described embodiments, but that it have the full scope defined by the language of the following claims, and equivalents thereof.

We claim:

1. An electrosurgical blade for conveying electrosurgical power to tissue to achieve a predetermined electrosurgical effect, comprising:
   an active electrode having a first section, a first tapered section terminating at a first conductor edge, and a first electrical coupling surface for electrically coupling the active electrode to a handle;
   a first outermost insulation layer having a second tapered section generally following the contours of and overlaying the active electrode which tapers against a side of the first tapered section to expose the first conductor edge;
   a return electrode electrically isolated from the active electrode, the return electrode having a third section, a third tapered section terminating at a second conductor edge, and a second electrical coupling surface for electrically coupling the return electrode to the handle;
   a second outermost insulation layer having a fourth tapered section generally following the contours of and overlaying the return electrode which tapers against a side of the third tapered section to expose the second conductor edge; and
   a passive electrode electrically isolated from the active electrode and the return electrode, the passive electrode having a third electrical coupling surface for electrically coupling the passive electrode to the handle.

2. The electrosurgical blade as recited in claim 1, wherein at least a portion of the thickness of the first conductor edge is less than that of the first section.

3. The electrosurgical blade as recited in claim 2 wherein the ratio of width of a first section to at least a portion of the first conductor edge is at least 5:1.

4. The electrosurgical blade as recited in claim 2 wherein the ratio of width of a first section to at least a portion of the first conductor edge is 20:1.

5. The electrosurgical blade as recited in claim 2, wherein at least a portion of the first conductor edge is flush against the first outermost insulation layer near the first conductor edge.

6. The electrosurgical blade as recited in claim 5, wherein at least a portion of the first tapered section includes a beveled surface.

7. The electrosurgical blade as recited in claim 6, wherein at least a portion of the first tapered section includes two beveled surfaces.

8. The electrosurgical blade as recited in claim 7, wherein at least a portion of the first tapered section has a concave shape.

9. The electrosurgical blade as recited in claim 8, wherein at least a portion of the second tapered section has a concave shape.

10. The electrosurgical blade as recited in claim 8, wherein at least a portion of the second tapered section of the first outermost section insulation layer has a linear taper shape.

11. The electrosurgical blade as recited in claim 5, wherein at least one side of the first tapered section extends radially inward.

12. The electrosurgical blade as recited in claim 11, wherein at least one side of the third tapered section extends radially inward.

13. The electrosurgical blade as recited in claim 12, wherein a tangent to the insulation of at least one of the first and second outermost insulation layers at a respective at least one of the first conductor edge and second conductor edge forms an angle with a centerline of the blade of less than about 45 degrees.

14. The electrosurgical blade as recited in claim 12, wherein a tangent to the insulation of at least one of the first and second outermost insulation layers at a respective at least one of the first conductor edge and second conductor edge forms an angle with a centerline of the blade of less than about 20 degrees.

15. The electrosurgical blade as recited in claim 1, wherein at least a portion of the first tapered section has a concave shape.

16. The electrosurgical blade as recited in claim 15, wherein at least a portion of the second tapered section has a concave shape.

17. The electrosurgical blade as recited in claim 15, wherein at least a portion of the third tapered section has a convex shape.

18. The electrosurgical blade as recited in claim 1, wherein a tangent to the insulation of at least one of the first and second outermost insulation layers at a respective at least one of the first conductor edge and second conductor edge forms an angle with a centerline of the blade of less than about 60 degrees.

19. The electrosurgical blade as recited in claim 1, wherein a tangent to the insulation of at least one of the first and second outermost insulation layers at a respective at least one of the first conductor edge and second conductor edge forms an angle with a centerline of the blade of less than about 45 degrees.

20. The electrosurgical blade as recited in claim 1, wherein a tangent to the insulation of at least one of the first and second outermost insulation layers at a respective at least one of the first conductor edge and second conductor edge forms an angle with a centerline of the blade of less than about 20 degrees.

21. The electrosurgical blade as recited in claim 1, wherein each of the first and second conductor edges has a thermal conductivity of at least 0.0002 W/° K at about 300° K.

22. The electrosurgical blade as recited in claim 1, wherein at least a portion of the first conductor edge has a transverse cross section that comes to approximately a point.

23. The electrosurgical blade as recited in claim 22, wherein at least a portion of the second conductor edge has a transverse cross section that comes to approximately a point.

24. The electrosurgical blade as recited in claim 1, wherein at least a portion of the first conductor edge has a transverse cross section that forms an acute angle.

25. The electrosurgical blade as recited in claim 24, wherein at least a portion of the second conductor edge has a transverse cross section that forms an acute angle.

26. The electrosurgical blade as recited in claim 1, wherein at least a portion of the first conductor edge has a thickness less than about 0.005 inches.

27. The electrosurgical blade as recited in claim 1, wherein at least a portion of the first conductor edge has a thickness less than about 0.002 inches.

28. The electrosurgical blade as recited in claim 1, wherein at least a portion of the first conductor edge has a thickness less than about 0.0005 inches.

29. The electrosurgical blade as recited in claim 1, wherein at least a portion of the thickness of each of the first and second insulation layers within a primary reaction region is at least one half the thickness of either the first or second conductor edge.

30. The electrosurgical blade as recited in claim 1, wherein the thickness of the first insulation layer a primary reaction region is at least as thick as the first conductor edge.

31. The electrosurgical blade as recited in claim 1, wherein the electrosurgical blade is configured for single use.

32. The electrosurgical blade according to claim 1, wherein the passive electrode is electrically isolated from the active electrode and the return electrode by an inner insulation layer.

33. The electrosurgical blade as recited in claim 1, wherein the passive electrode extends along a centerline of the instrument.

34. The electrosurgical blade as recited in claim 1, wherein the first tapered section, second tapered section, third tapered section and fourth tapered section converge to form an instrument edge.

35. A sterile package kit for use in performing an electrosurgical procedure, comprising:
 a sterile package; and
 a single use electrosurgical blade sealed within the sterile package, the single use electrosurgical blade comprising:
 an active electrode having a first section, a first tapered section terminating at a first conductor edge, and a first electrical coupling surface for electrically coupling the active electrode to a handle;
 a first outermost insulation layer having a second tapered section generally following the contours of and overlaying the active electrode which tapers against a side of the first tapered section to expose the first conductor edge;
 a return electrode electrically isolated from the active electrode, the return electrode having a third section, a third tapered section terminating at a second conductor edge, and a second electrical coupling surface for electrically coupling the return electrode to the handle;
 a second outermost insulation layer having a fourth tapered section generally following the contours of and overlaying the return electrode which tapers against a side of the third tapered section to expose the second conductor edge; and
 a passive electrode electrically isolated from the active electrode and the return electrode, the passive electrode having a third electrical coupling surface for electrically coupling the passive electrode to the handle.

36. The sterile package kit according to claim 35, further comprising the handle sealed within the sterile package.

37. The sterile package kit according to claim 35, further comprising printed instructions informing a user how to couple the single use electrosurgical blade to the handle.

38. The electrosurgical blade according to claim 35, wherein the passive electrode is electrically isolated from the active electrode and the return electrode by an inner insulation layer.

39. The sterile package kit according to claim 35, wherein the passive electrode extends along a centerline of the instrument.

40. The sterile package kit according to claim 35, wherein the first tapered section, second tapered section, third tapered section and fourth tapered section converge to form an instrument edge.

* * * * *